US008784913B2

(12) United States Patent
Berry et al.

(10) Patent No.: US 8,784,913 B2
(45) Date of Patent: Jul. 22, 2014

(54) REHYDRATABLE FOOD

(75) Inventors: Mark John Berry, Sharnbrook (GB); John Casey, Sharnbrook (GB); Ravine Anthony Gungabissoon, Sharnbrook (GB); Andrew Paul Ormerod, Sharnbrook (GB); Sally Pamela Redfern, Sharnbrook (GB); Jacqueline de Silva, Sharnbrook (GB); Joy Elizabeth Wilkinson, Sharnbrook (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 13/698,680

(22) PCT Filed: May 25, 2011

(86) PCT No.: PCT/EP2011/058539

§ 371 (c)(1), (2), (4) Date: Nov. 19, 2012

(87) PCT Pub. No.: WO2011/154253

PCT Pub. Date: Dec. 15, 2011

(65) Prior Publication Data

US 2013/0101701 A1 Apr. 25, 2013

(30) Foreign Application Priority Data

Jun. 8, 2010 (EP) .................................... 10165272

(51) Int. Cl.

| | |
|---|---|
| ***A23L 1/212*** | (2006.01) |
| ***C12N 15/82*** | (2006.01) |
| ***A23L 1/305*** | (2006.01) |
| ***A23B 7/022*** | (2006.01) |
| ***A23B 7/02*** | (2006.01) |

(52) U.S. Cl.

CPC ............. *A23L 1/212* (2013.01); *C12N 15/8242* (2013.01); *A23L 1/2121* (2013.01); *A23L 1/305* (2013.01); *A23B 7/022* (2013.01); *A23B 7/02* (2013.01)

USPC ............. 426/61; 426/640; 426/541; 426/545; 426/547; 426/542; 426/637; 426/597; 426/638; 426/616; 426/589; 426/590; 426/620; 426/583; 426/465; 530/370

(58) Field of Classification Search

None

See application file for complete search history.

(56) References Cited

U.S. PATENT DOCUMENTS 4,781,937 A 11/1988 Knowles et al.

FOREIGN PATENT DOCUMENTS

| | | | |
|---|---|---|---|
| CN | 101591383 | A | 12/2009 |
| WO | WO9703575 | A1 | 2/1997 |
| WO | WO2005122697 | A2 | 12/2005 |

OTHER PUBLICATIONS

Serrano et al., Molecular Bases of Desiccation Tolerance in Plant Cells and Potential Applications in Food Dehydration, Food Sci Tech Inst, 2003, 157-162, 9(3), Sage Publications.

Uniprot Consortium, Database—Uniprot (Online), Uniprot B5TV66 Squence Listing, Nov. 4, 2008, 1-2.

Uniprot Consortium, Database Uniprot (Online), Uniprot B7U647 Squence Listing, Feb. 10, 2009, 1-2.

European Search Report for Application No. EP10165272 dated Nov. 17, 2010.

International Search Report for International Application No. PCT/EP2011/058539 with Written Opinion completed Nov. 15, 2011.

Roberts et al., "Cellular Concentrations and Uniformity of Cell-Type Accumulation of Two Lea Proteins in Cotton Embryos", The Plant Cell, 1993, vol. 5, 769-780.

Close, "Dehydrins: A commonalty in the response of plants to dehydration and low temperature", Physiologia Plantaarum 1997, 100, 291-296.

Close et al, A view of plant dehydrins using antibodies specific to the carboxy terminal peptide, Plant Molecular Biology, 1993, 279-286, 23, US.

Close, Dehyrins: Emergence of a biochemical role of a family plant dehydration proteins,Physiologia Plantarium, 1996, 795-803, 97, US.

Koag et al, The binding of Maize DHN1 to Lipid vesicles. Gain of structure and lipid specificty. Plant Physiology, 2003, 309-316, 131, US.

Xiaohong et al., Application of cDNA Library in Research of Plant Drought Resistance Mechanism, Biotechnology Bulletin, Dec. 31, 2009, 57-60, 3.

Zhang et al., Dehydration-induced intracellular solute changes and acquisition of plant desiccation tolerance, Journal of Plant Physiology and Molecular Biology, Dec. 31, 2007, 9-17, 33 1.

*Primary Examiner* — Karlheinz R Skowronek
*Assistant Examiner* — Schuyler Milton
(74) *Attorney, Agent, or Firm* — Michael P. Aronson

(57) ABSTRACT

Use of dried rehydratable food, such as in a dried soup, a dried beverage, a breakfast cereal, a yoghurt and a dried sauce, is widespread. However it has been observed that when the dried components are fruit and/or vegetable, the components, on rehydration, do not resemble the fruit and/or vegetable before desiccation. That is to say they no longer have a fresh appearance but are discoloured and lack firmness. This transformation is due to cellular damage which occurs during desiccation. In particular, it is thought that phospholipid membranes are destabilised by insertion of cellular amphiphiles, phase transition into the gel phase and membrane fusion. This invention seeks to solve the above-mentioned technical problem by providing, amongst other things, a dried rehydratable food which is a fruit, vegetable or part thereof which, on rehydration, has improved appearance, texture and rehydration properties. In particular, a dried rehydratable food is provided, the food comprising less than 10% w/w water and at least 0.02% w/w of a dehydrin protein and derivatives thereof, the dehydrin protein and derivatives thereof comprising an amino acid sequence selected from the group consisting of K,I,K,E,K,L,P,G; K,I,K,E/D,K,L/I,P,G; and K,I,K,E/D,K,L/I/TA/,P/H/S,G, and wherein the dried rehydratable food is unbroken tissue of a vegetable or part thereof and/or a fruit or part thereof, and not a seed, wherein the unbroken tissue has a shortest linear dimension of at least 0.5 millimeters, preferably a shortest linear dimension of 0.5 to 25, more preferably 0.5 to 10 millimeters. A food product comprising the dried rehydratable food and methods for manufacturing the dried rehydratable food are also provided.

18 Claims, 13 Drawing Sheets

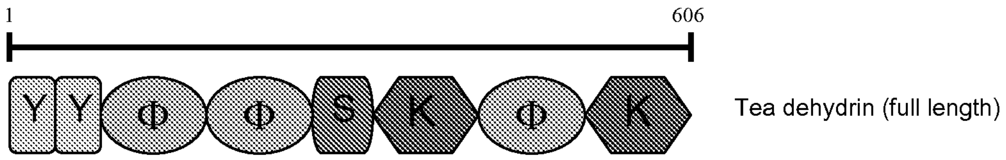

Figure 3a

```
  1                                                 M  A  H  N  S  N  Q  Y
  1                                                 ATGGCACATAACAGCAACCAAT
  9   G  N  P  P  R  Q  T  D  E  Y  G  N  P  P  R  K  T  D  E  F
 23 ATGGGAACCCACCTCGCCAAACTGACGAGTATGGAAACCCACCTCGCAAAACCGACGAGT
 29   G  D  P  V  R  Q  I  D  E  Y  G  N  P  V  H  H  T  G  T  M
 83 TTGGTGACCCAGTTCGCCAAATTGACGAGTACGGAAACCCGGTTCACCATACTGGTACCA
 49   G  D  Y  G  T  T  T  G  T  T  G  V  H  G  T  H  T  G  T  T
143 TGGGAGATTATGGTACCACTACCGGTACCACAGGTGTTCATGGCACCCACACCGGCACTA
 69   G  T  Y  G  T  G  T  T  G  T  Y  G  T  G  M  D  T  T  G  T
203 CGGGCACTTATGGCACCGGCACTACTGGCACTTATGGCACCGGGATGGATACCACCGGTA
 89   T  G  T  H  G  L  S  T  G  T  G  G  H  H  Q  Q  H  A  D  G
263 CCACTGGTACCCATGGTTTGAGCACTGGTACCGGAGGCCATCATCAGCAGCATGCTGACG
109   G  V  L  H  R  S  G  S  S  S  S  S  S  E  D  D  G  Q  G  G
323 GAGGAGTGCTTCACCGCTCCGGCAGCAGCTCTAGCTCTTCAGAGGATGATGGTCAAGGAG
129   R  R  K  K  K  G  L  T  Q  K  I  K  E  K  L  P  G  G  H  K
383 GGAGGAGGAAGAAGAAAGGGCTGACACAGAAGATAAAGGAGAAGCTGCCAGGTGGGCACA
149   D  Q  T  P  Q  Y  D  N  T  T  T  T  P  G  A  A  T  T  G  G
443 AAGACCAGACACCGCAGTACGACAACACAACCACCACTCCAGGAGCAGCCACCACCGGTG
169   Y  G  Y  G  G  E  D  Q  Q  Q  Y  P  E  K  K  G  M  M  E  K
503 GCTATGGCTACGGAGGAGAGGACCAACAGCAGTACCCTGAAAAGAAAGGAATGATGGAGA
189   I  K  E  K  L  P  G  H  T  T  T  N  K
563 AGATCAAGGAGAAGCTTCCTGGCCACACCACCACTAATAAATAA
```

Figure 3b

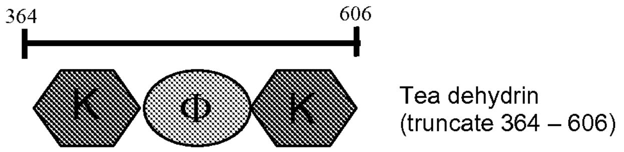

Figure 4a

```
122                                                     E   D   D   G   Q   G   G
364                                                     GAGGATGATGGTCAAGGAG
129   R   R   K   K   K   G   L   T   Q   K   I   K   E   K   L   P   G   G   H   K
383 GGAGGAGGAAGAAGAAAGGGCTGACACAGAAGATAAAGGAGAAGCTGCCAGGTGGGCACA
149   D   Q   T   P   Q   Y   D   N   T   T   T   T   P   G   A   A   T   T   G   G
443 AAGACCAGACACCGCAGTACGACAACACAACCACCACTCCAGGAGCAGCCACCACCGGTG
169   Y   G   Y   G   G   E   D   Q   Q   Q   Y   P   E   K   K   G   M   M   E   K
503 GCTATGGCTACGGAGGAGAGGACCAACAGCAGTACCCTGAAAAGAAAGGAATGATGGAGA
189   I   K   E   K   L   P   G   H   T   T   T   N   K
563 AGATCAAGGAGAAGCTTCCTGGCCACACCACCACTAATAAATAA
```

Figure 4b

```
163                                                    A  A  T  T  G  G
487                                                    GCAGCCACCACCGGTG
169   Y  G  Y  G  G  E  D  Q  Q  Q  Y  P  E  K  K  G  M  M  E  K
503 GCTATGGCTACGGAGGAGAGGACCAACAGCAGTACCCTGAAAAGAAAGGAATGATGGAGA
189   I  K  E  K  L  P  G  H  T  T  T  N  K
563 AGATCAAGGAGAAGCTTCCTGGCCACACCACCACTAATAAATAA
```

```
  1 CTGCACTACTGAACAAACTTAGAAGTTGAACAATAGCTTGTTATTTGAGT

 51 TTTGATAAACATTTGAAATTAGAAGAAATGGAGCAGTACGGGGACCAACA
  1                                  M  E  Q  Y  G  D  Q  H
101 CGGCAACCAGATACGCAAGACTGACGAATATGGAAACCCTGTTCAACACA
  9  G  N  Q  I  R  K  T  D  E  Y  G  N  P  V  Q  H
151 CTGGAAAACAAGGAACTGGTCAAGGTGGAATTGCTCCAGGCACCCTTGAT
 25 T  G  K  Q  G  T  G  Q  G  G  I  A  P  G  T  L  D
201 GCTGGCCTAGCTGGGCAGCAACATGGCCAGCTCCGCCGCTCTGGCAGCTC
 42  A  G  L  A  G  Q  Q  H  G  Q  L  R  R  S  G  S  S
251 GTCGTCAGAGGATGATGGGCTAGGTGGGAGGAGAAAGAAGGGGATGAAGG
 59  S  S  E  D  D  G  L  G  G  R  R  K  K  G  M  K
301 ACAAGATAAAGGAGAAGTTGCCTGGGGGGCACAAGGATGAGCAGAATTAC
 75 D  K  I  K  E  K  L  P  G  G  H  K  D  E  Q  N  Y
351 GGGACTCAAACAACTACACCTGCAGGAGGCTACGGATGTGGTGGAGGAGA
 93  G  T  Q  T  T  T  P  A  G  G  Y  G  C  G  G  G  E
401 GCATCAGGAGAAGAAGGGAGTGGTGGAAAAGATCAAGGAGAAGCTGCCTG
110  H  Q  E  K  K  G  V  V  E  K  I  K  E  K  L  P
451 GAGGCGGCCACTAGATCACATCACTATGTTTCTAATAATGTTTTATACTA
126 G  G  G  H
501 TGTTGTCTTTAAAGTTTTAAGACATGCGTCTGAGTCGAGTTTATG
```

Figure 6

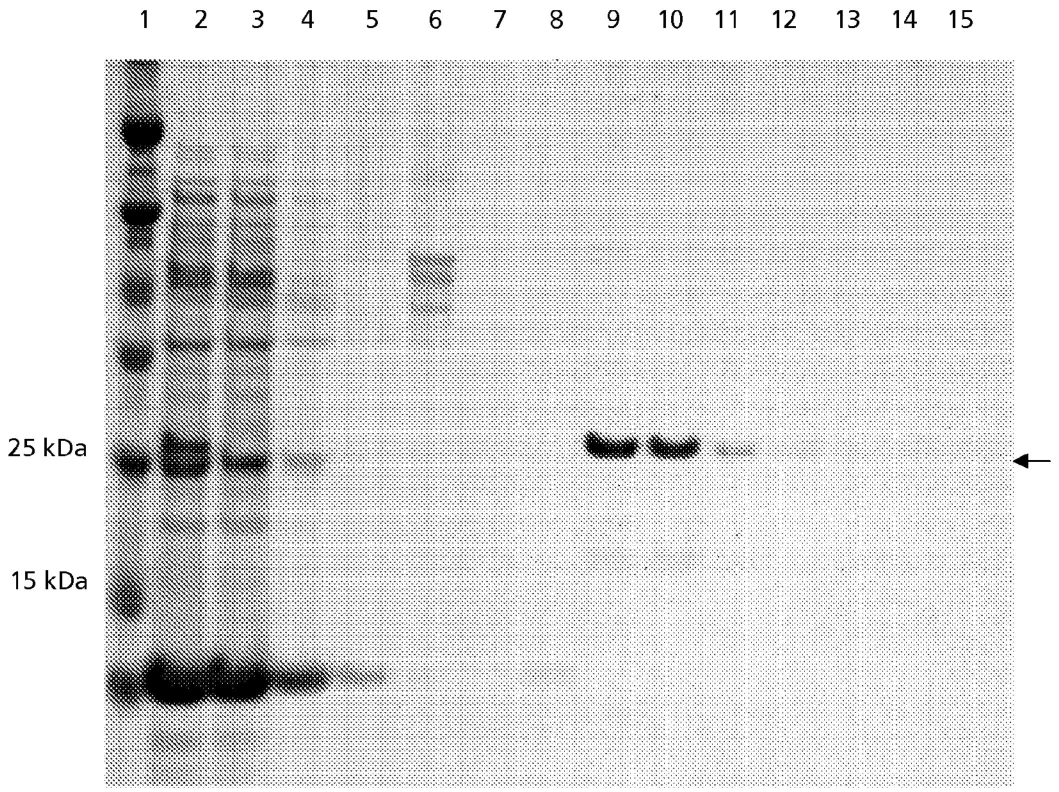

Figure 7

REHYDRATABLE FOOD

This invention relates to dried rehydratable food, in particular to a food which is a fruit, vegetable or part thereof. This invention also relates to methods of manufacture thereof and a food product, such as a dried soup, a dried beverage, a breakfast cereal, a yoghurt and a dried sauce, comprising the aforementioned dried rehydratable food.

Use of dried rehydratable food, such as in a dried soup, a dried beverage, a breakfast cereal, a yoghurt and a dried sauce, is widespread. However it has been observed that when the dried components are fruit and/or vegetable, the components, on rehydration, do not resemble the fruit and/or vegetable before desiccation. That is to say they no longer have a fresh appearance but are discoloured and lack firmness. This transformation is due to cellular damage which occurs during desiccation. In particular, it is thought that phospholipid membranes are destabilised by insertion of cellular amphiphiles, phase transition into the gel phase and membrane fusion.

Serrano et al (Food Sci. Tech. Int., 9(3), 157-161 (2003)) discusses potential applications to food dehydration and discloses that it has been observed that late embryogenesis abundant (LEA) proteins are abundant at high levels during the maturation process of seed embryogenesis and also in all plant tissues experiencing water stress. LEA proteins comprise, amongst others, the dehydrins. The authors state that LEA proteins may stabilise proteins and membranes during desiccation by a similar mechanism to osmolytes. That is by conferring preferential hydration of the cellular structures, then actually replacing water during desiccation. Osmolytes also contribute to osmotic adjustment and act as efficient hydroxyl radical scavengers during desiccation. The authors also disclose that three biological systems seem to act in concert to achieve desiccation tolerance: enzymes involved in osmolyte synthesis; proteins specialised in desiccation protection of membranes and proteins (LEA proteins); and antioxidant enzymes and molecules.

This invention seeks to solve the above-mentioned technical problem by providing, amongst other things, a dried rehydratable food which is a fruit, vegetable or part thereof which, on rehydration, has improved appearance, texture and rehydration properties.

SUMMARY OF THE INVENTION

In a first aspect of the invention, a dried rehydratable food is provided, the food comprising less than 10% w/w water and at least 0.02% w/w of a dehydrin protein and derivatives thereof, the dehydrin protein and derivatives thereof comprising an amino acid sequence 5 selected from the group consisting of KIKEKLPG (SEQ ID No. 14); KIKE/DKL/IPG (SEQ ID No. 15); and KIKE/DKL/I/T/VP/H/SG (SEQ ID No. 16), and wherein the dried rehydratable food is unbroken tissue of a vegetable or part thereof and/or a fruit or part thereof, and not a seed, wherein the unbroken tissue has a shortest linear dimension of at least 0.5 millimeters, preferably a shortest linear dimension of 0.5 to 25, more preferably 0.5 to 10 millimeters.

By the term “rehydratable” is meant that the food may be rehydrated to at least 50%, preferably at least 60%, most preferably at least 70% w/w of the water content of a fully hydrated vegetable or part thereof and/or fruit or part thereof. Preferably the term “rehydratable” means that the food may be rehydrated to no more than 99%, preferably no more than 97%, most preferably no more than 95% w/w of the water content of a fully hydrated vegetable or part thereof and/or fruit or part thereof.

Derivatives thereof include glycosylated dehydrins and truncated dehydrins, wherein truncated dehydrins still contain the critical K segment (see below).

Adjacent positions in the amino acid sequence are separated by a comma and the most frequently observed amino acid listed first with each amino acid at a single position separated by a forward slash.

The inventors have surprisingly observed that by raising the concentration of dehydrin proteins in fruit and/or vegetable tissue above that found naturally, dried rehydratable food is obtained which on rehydration has improved appearance, texture and rehydration properties. Whilst the prior art does suggest that LEA proteins may play a role in protecting plants from water stress, it is surprising that the use of dehydrin alone has resulted in this improvement in the aforementioned performance properties of dried rehydratable fruit and/or vegetable because three biological systems seem to act in concert to achieve desiccation tolerance.

From data provided by Roberts et al. (The Plant Cell, 5, 769-780 (1993)), it has been calculated that seeds can comprise about 0.5% of dry weight levels of dehydrin. There is, however, no consensus in the literature as to why the levels are this high. Seeds, as such, are not the subject of the invention and are therefore excluded.

Preferably the dried rehydratable food comprises 0.02 to 20, preferably 0.1 to 5, most preferably 0.2 to 2.5% w/w dehydrin protein and derivatives thereof. Natural levels of dehydrin protein are below 0.02% w/w. The dehydrin protein and derivatives thereof preferably have a molecular weight of 1 to 150, preferably 5 to 100, most preferably 5 to 50 kD. Dehydrin proteins and derivatives thereof of lower molecular weight are preferable because they more easily infuse into the fruit or vegetable tissue.

The dehydrin and derivatives thereof are preferably derived from the group consisting of *Camellia sinensis, Forsythia* and *Selaginella*, more preferably from *Camellia sinensis*, in particular with an amino acid sequence at least 80% identical to SEQ ID NO:1 (see FIG. 3*b*), preferably at least 90%, 95% or 99% identical thereto. It was observed that the dehydrin of SEQ ID NO:1 was 47× up-regulated when tea plant tissue was withered, therefore it was postulated that this particular dehydrin had an important role to play in protecting the plant tissue during desiccation. This has subsequently been proven to be the case from the results set forth hereinafter in the detailed description of the invention.

Another preferred *Camellia sinensis* derived dehydrin protein (a truncate form) has an amino acid sequence at least 80% identical to SEQ ID NO:2 (see FIG. 4*b*), preferably at least 90%, 95% or 99% identical thereto.

Yet another preferred *Camellia sinensis* derived dehydrin protein (another truncate form) has an amino acid sequence at least 80% identical to SEQ ID NO:3 (see FIG. 5*b*), preferably at least 90%, 95% or 99% identical thereto.

It was thought that truncated versions of tea dehydrin SEQ ID NO:1 still containing the critical K segment (see below) and labelled SEQ ID NO:2 and SEQ ID NO:3 would infuse more easily and deeply into fruit and/or vegetable tissue and thus provide enhanced protective activity when compared to the full length form (SEQ ID NO:1). The truncated versions may also have a higher functional activity as some of the regulatory areas of the protein would be removed.

The rehydratable food may additionally comprise a compound selected from the group consisting of trehalose, sucrose, glucose, fructose, raffinose, an enzymatic antioxidant or a non-enzymatic reactive oxygen species scavenger. The foregoing species are thought to be able to protect, by a variety of different mechanisms, the integrity of the fruit or vegetable tissue when it undergoes dehydration. For example the sugars are thought to protect cell membranes during desiccation firstly by inducing preferential hydration of the cellular structures, then by actually replacing water protecting the cellular structure. Also the sugars may act as efficient hydroxyl radical scavengers controlling the increased production of reactive oxygen species seen during desiccation. Cellular electron transport chains are impaired upon dehydration and hence generate increasing amounts of reactive oxygen intermediates. Thus enzymatic antioxidant or a non-enzymatic reactive oxygen species scavenger would be expected to improve the ability of fruit or vegetable tissue to resist desiccation with reduced cellular damage. Suitable enzymatic antioxidants include catalase, superoxide dismutase, ascorbate peroxidase and glutathione reductase. Suitable non-enzymatic reactive oxygen species scavengers include ascorbate, glutathione and carotenoids.

The vegetable may be selected from the group consisting of spinach, broccoli, onion, aubergine, courgette, potato, pumpkin, mushroom, carrot, tea, asparagus, turnip, leek, beetroot, cauliflower, celeriac, artichoke, mint, thyme, oregano, rosemary, parsley, sage, chives, marjoram, basil, bay leaf, tarragon, celery and garlic and the fruit may be selected from the group consisting of lemon, raspberry, red currant, blackberry, berry, blueberry, strawberry, pineapple, banana, peach, apricot, lychee, apple, pear, tomato, *capsicum*, cucumber and mango.

In a second aspect of the invention, a food product is provided, the food product comprising a dried rehydratable food according to the first aspect of the invention. The food product may be selected from the group consisting of a dried soup, a dried beverage, a breakfast cereal, a yoghurt and a dried sauce. All of the foregoing food products are characterised in including a dried fruit or vegetable component which is rehydrated on use.

In a third aspect of the invention, a method for manufacturing a dried rehydratable food according to the first aspect of the invention, the method comprising the steps of:

(a) Infusing a vegetable or part thereof, or a fruit or part thereof excluding a seed, with a dehydrin protein and derivatives thereof, the dehydrin protein and derivatives thereof comprising an amino acid sequence selected from the group consisting of KIKEKLPG (SEQ ID NO:14); KIKE/DKL/IPG (SEQ ID NO:15); and KIKE/DKL/I/T/VP/H/SG (SEQ ID NO:16) to produce an infused food; and (b) Drying the infused food thereby to produce a dried rehydratable food according to the first aspect of the invention.

The surprising observation of the third aspect of the invention is the fact that a dried rehydratable food is obtained which on rehydration has improved appearance, texture and rehydration properties by simple diffusion of dehydrin into the fruit and/or plant tissue.

Preferably step (a) of the third aspect of the invention is carried out under a vacuum. It is anticipated that under vacuum, infusion is faster. Step (a) of the third aspect of the invention may be carried out at a temperature of 3 to 70, preferably 10 to 50, most preferably 15 to 30 degrees centigrade. At too low a temperature, the infusion process is too slow, and at too high a temperature, the tissue structure is damaged.

In a fourth aspect of the invention, a method for manufacturing a dried rehydratable food according to the first aspect of the invention is provided, the method comprising the steps of:

(a) Cloning a gene into a plant expression vector thereby to produce a modified plant expression vector, wherein the gene encodes a dehydrin protein and derivatives thereof, wherein the dehydrin protein and derivatives thereof comprises an amino acid sequence selected from the group consisting of KIKEKLPG (SEQ ID NO:14); KIKE/DKL/IPG (SEQ ID NO:15); and KIKE/DKL/I/T/VP/H/SG (SEQ ID NO:16);

(b) Introducing the modified plant expression vector into a target crop by plant transformation thereby to produce a transgenic target crop;

(c) Growing the transgenic target crop thereby to express the dehydrin protein and derivatives thereof; and then (d) Drying the transgenic target crop thereby to produce a dried rehydratable food according to the first aspect of the invention.

In a fifth aspect of the invention is provided a dehydrin protein with an amino acid sequence identical to SEQ ID NO:1, and derivatives thereof.

In a sixth aspect of the invention is provided a dehydrin protein with an amino acid sequence identical to SEQ ID NO:2, and derivatives thereof.

In a seventh aspect of the invention is provided a dehydrin protein with an amino acid sequence at least 80% identical to SEQ ID NO:4, preferably at least 90%, 95% or 99% identical thereto, and derivatives thereof.

BRIEF DESCRIPTION OF THE FIGURES

The invention will now be exemplified with reference to the following figures in which:

FIG. 3 shows a tea dehydrin gene in schematic form in FIG. 3*a* and in the form of a nucleotide and deduced amino acid sequence in FIG. 3*b* (SEQ ID NO:1);

FIG. 4 shows the tea dehydrin of FIG. 3 in truncated form (truncate 122-201 of SEQ ID NO:1) in schematic form in FIG. 4*a* and in the form of a nucleotide and deduced amino acid sequence in FIG. 4*b* (SEQ ID NO:2);

FIG. 6 shows the nucleotide and deduced amino acid sequence (SEQ ID NO:4) of the *Forsythia suspensa* dehydrin gene;

FIG. 7 shows SDS-PAGE gel plate of recombinant tea dehydrin wherein the arrow indicates the position of the dehydrin fusion protein band, column (1) the molecular weight markers (kiloDaltons), column (2) the cell lysate supernatant of IPTG induced *E. coli* harbouring the pDEST 17-dehydrin construct, column (3) unbound proteins eluted from the Ni-NTA column after sample addition, columns (4) to (8) the contaminant proteins eluted after successive column washes, and columns (9) to (15) the fractions collected following Elution Buffer application;

DETAILED DESCRIPTION OF THE INVENTION

Figure 1:
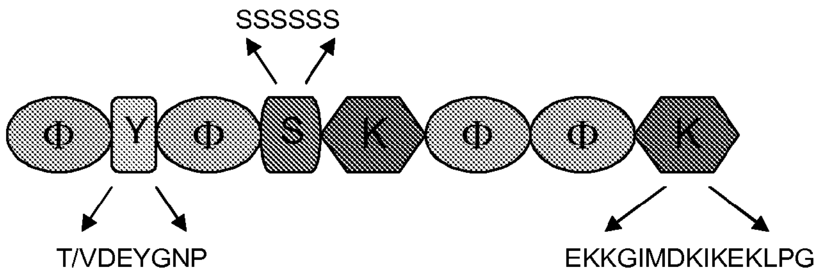
FIG. 1 shows the characteristic structure of a generalised dehydrin protein molecule showing conserved sequence motifs wherein the Y segment is typically located towards the nitrogen terminus, the $\phi$ segments are repeated regions mostly made up of glycine and polar amino acids, the S segment contains a tract of phosphorylatable serine residues and the K segment is rich in lysine and constitutes the putative amphipathic $\alpha$-helix forming domain (the sequences of letters refer to the corresponding amino acid sequence)

Dehydrin genes are composed of distinct domains that exhibit high levels of conservation across plant species. FIG. 1 shows a schematic diagram of the generalised architecture of dehydrins. Each protein is comprised of multiple copies of K, ϕ, S and Y segments. For example, the K segment can occur up to 11 times per polypeptide whereas the Y segment is normally found in 1 to 3 tandem repeats near the N-terminus. The four main segments are interspersed by other lesser conserved and usually repeated regions. The strict conservation of the K, ϕ, S and Y segments during evolution indicates that they define functional units within these proteins. Dehydrins can be characterized by the KIKEKLPG (SEQ ID NO:15) amino acid sequence found near the carboxy terminus which is usually repeated within the protein. This amino acid sequence forms part of the K segment. More generally the carboxy terminal peptide of dehydrins that emerges from an alignment of available published data is: EKKG/SI/V/M/L/FM/L/VD/EKIKE/DKL/IPG (SEQ ID NO:17).

Example 1

Extraction and Purification of Resurrection Plant *Selaginella lepidophylla* Dehydrin Protein extracts from *Selaginella lepidophylla* were probed with a dehydrin anti-body to detect dehydrin-like proteins in *Selaginella lepidophylla* (a type of Resurrection plant which is a plant known for showing remarkable tolerance to drought) tissues. Once identified the proteins were purified by ion exchange chromatography.

a) Preparation of Whole Protein Extract from *Selaginella lepidophylla* Tissue

A fully hydrated entire *Selaginella lepidophylla* plant which had been dehydrated at room temperature for five hours (so it is partially dehydrated) was ground to a flour-like consistency in a coffee grinder. The powder was suspended at a concentration of 200 g/L in a pre-chilled (4 degrees centigrade) pH 6.0 extraction buffer containing 25 mM 2-(N-morpholino)ethanesulfonic acid (MES), 20 mM NaCl and 1 mM phenylmethylsulfonyl fluoride (PMSF). The suspension was stirred for 3 hours at 4 degrees centigrade before being mixed in a blender for 1 minute after which the homogenate was stirred for a further 12 hours at 4 degrees centigrade. Insoluble material was pelleted by centrifugation at 10,000 rpm for 30 minutes at 4 degrees centigrade. The supernatant was subsequently filtered through two separate layers of cheesecloth. Non-heat stable proteins were denatured by incubation at 70 degrees centigrade for 10 minutes with occasional shaking. The solution was rapidly cooled on ice and filtered through Whatman Paper No. 1. Any remaining insoluble material was pelleted by centrifugation at 30,000 rpm for 1 hour.

b) Detection of Dehydrin Proteins in *Selaginella lepidophylla* Whole Protein Extracts by Western Blotting A ~20 μL aliquot of *Selaginella lepidophylla* total protein extract was loaded onto an electrophoresis gel (12% Novex bis(2-hydroxyethyl)iminotris(hydroxymethyl)methane (bis-tris)) and run for approximately 40 minutes at 200V in a MES and sodium dodecyl sulphate (SDS) running buffer. The proteins on the gel were blotted onto a nitrocellulose sheet for 1 hour at 30 V. Unbound sites on the nitrocellulose were blocked by immersion in tris(hydroxymethyl)aminomethane (tris) buffered saline (TBS) containing 5% dried milk powder (blocking buffer) for 1 hour. The blot was then incubated in rabbit polyclonal dehydrin anti-serum (Stressgen Bioreagents) diluted 1:1000 in the blocking buffer for 1 hour. Following four consecutive 5 minutes washes with TBS containing 0.05% polysorbate 20 (Tween 20), the nitrocellulose was soaked in alkaline phosphatase conjugated goat anti-rabbit antibody (Invitrogen). After four consecutive 5 minute washes with TBS containing 0.05% polysorbate 20 (Tween 20), conjugate bound dehydrin was detected by the addition of 5 mL 5-bromo-4-chloro-3-indolyl phosphate/nitro blue tetrazolium (BCIP/NBT) solution (Sigma).

c) Purification of Dehydrin Protein from *Selaginella lepidophylla* Tissue Whole Protein Extracts.

Figure 2:
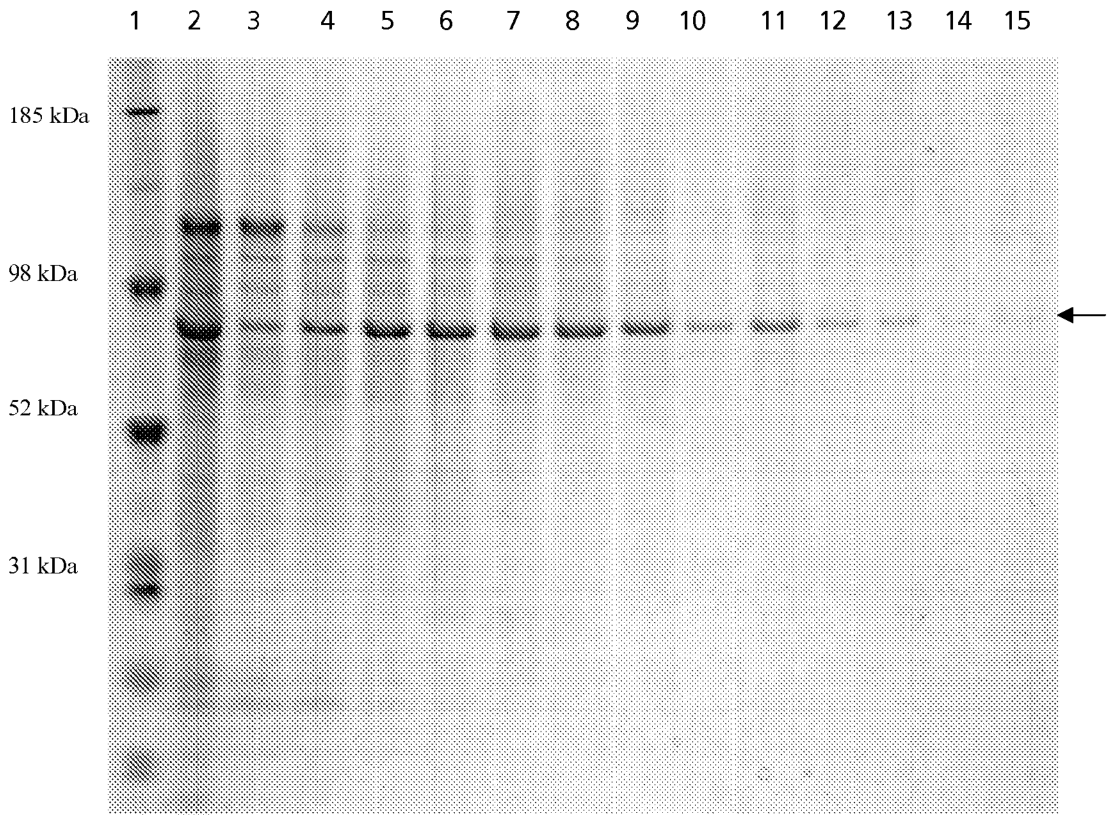
FIG. 2 shows a sodium dodecyl sulphate/polyacrylamide gel electrophoresis (SDS-PAGE) plate of *Selaginella lepidophylla* dehydrin fractions following purification by a DEAE-Sepharose CL-6B ion exchange column where column (1) are the molecular weight marker (in kiloDaltons), column (2) is the total *Selaginella lepidophylla* extract and columns (3) to (15) are the fractions of the extract eluted with a 0.02 M:1 M KCl gradient (the arrow indicates the position of the dehydrin band)

20 mL *Selaginella lepidophylla* total protein extract was dialysed over night in 10 mM tris.HCl, 1 mM ethylene glycol tetraacetic acid (EGTA), 1 mM dithiothreitol (DTT) pH 8.0 buffer at 4 degrees centigrade. A 20 mL diethylaminoethyl cross-linked agarose based ion exchange column (DEAE-Sepharose CL-6B) was equilibrated with 500 mL of the same buffer. The dialysed extract was passed through the column at a rate of approximately 1 drop per second. Following sample addition the column was washed with 20 mL of column buffer. Proteins were then eluted in 4 mL fractions by the application of a 100 mL 0.02M:1 M KCl gradient. Pure dehydrin containing fractions were identified by sodium dodecyl sulphate/polyacrylamide (SDS-PAGE) gel electrophoresis, illustrated in FIG. 2, and fractions 9 to 15 (containing pure dehydrin) pooled.

Example 2

Isolation of *Camellia sinensis* Dehydrin cDNA, Cloning of Full Length and Truncated Dehydrin Sequences and Expression and Purification of Recombinant Dehydrin Proteins in *E. coli*

The procedure involved the following steps:

(a) A complementary deoxyribonucleic acid (cDNA) library was constructed from withered and non-withered tea shoots (*Camellia sinensis*);

(b) cDNA for a tea dehydrin contig present only in the withered cDNA library and represented by 47 independent cDNA clones (more than any other dehydrin detected) was selected;

(c) The selected cDNA dehydrin sequence was cloned into the *Escherichia coli* (*E. coli*) expression vector pDEST17 and transformed into *E. coli;*

(d) The transformed *E. coli* was multiplied in culture and induced to express the corresponding tea dehydrin protein;

(e) The *E. coli* cells were lysed and the expressed dehydrin protein purified using nickel ion-nitrolotriacetic acid resin (Ni-NTA); and (f) The purified dehydrin was dialysed with water prior to use.

Total RNA Isolated from Withered Tea Shoots

Tea shoots (two leaves and a bud) from *Camellia sinensis* variety assamica were harvested and withered for 19 hours (in a partially sealed plastic bag). Total ribonucleic acid (RNA) was isolated using a plant RNA isolation kit (Qiagen) in accordance with the manufacturer's instructions.

Synthesis of cDNA from mRNA to form cDNA Library mRNA was purified from 500 μg total RNA using a polyadenylic acid isolation kit (Qiagen) in accordance with the manufacturer's instructions. 5 μg of the polyadenylic acid-mRNA molecule was heated to 72 degrees centigrade for 5 minutes together with 2.8 μg polyadenylic acid linker primer containing an Xho1 restriction site (Stratagene), then snap cooled on ice for two minutes. The mRNA was reverse transcribed in a 50 μL reaction for 60 minutes at 42 degrees centigrade after an initial incubation at room temperature for 10 minutes, using 75 units of reverse transcriptase (Stratascript RT from Stratagene) in 1×RT buffer (Stratagene), 2.5 mM deoxyribonucleotide triphosphates (dNTP's) (comprising deoxyadenosine triphosphate (dATP), thymidine triphosphate (dTTP), 5-methyl deoxycytidine triphosphate and deoxyguanosine triphosphate (dGTP)) (Amersham-Pharmacia) and 40 units ribonuclease (RNAse) block (Stratagene).

Second strand cDNA was synthesised using 45 μL of the first strand synthesis reaction in a 200 μL reaction for 150 minutes at 16 degrees centigrade by adding 11 μL DNA polymerase 1 (9 units/μl) (Stratagene), 20 μL 10× second strand synthesis buffer (Stratagene), 6 μL dNTP's (40 mM) (Amersham-Pharmacia) and 2 μL RNAse H (1.5 units/μL) (Stratagene). 180 μL of the second strand synthesis reaction was blunted for 30 minutes at 72 degrees centigrade by adding 20.7 μL dNTP's (10 mM) and 1.8 μl cloned Pfu DNA polymerase (Stratagene) (an enzyme found in the hyperthermophilic archaeon *Pyrococcus furiosus*) (2.5 units/μL). The reaction was terminated by extracting once with an equal volume of 1:1 v/v phenol/chloroform and once with an equal volume of chloroform before precipitating the cDNA overnight at −20 degrees centigrade with 0.1 volume of 3M sodium acetate solution (pH 5.2) and 2 volumes of ethanol. The cDNA was resuspended in 9 μL EcoR1 (an endonuclease enzyme isolated from strains of *E. coli*) adapters (Stratagene) and incubated at 8 degrees centigrade overnight with 4 units of T4 DNA ligase (Stratagene) (T4 is a bacteriophage of *E. coli*) in 1× ligase buffer (Stratagene)+1 mM ribonucleotide ATP (rATP) (Stratagene). The ligation reaction was terminated by heating to 70 degrees centigrade for 30 minutes and then snap cooled on ice for two minutes. The cDNA ends were then phosphorylated in a 22 μl reaction at 37 degrees centigrade for 30 minutes by adding 1 μl T4 polynucleotide kinase (10 units/μl) (Stratagene), 1 μl ligase buffer (10×) and 1 μl rATP (10 mM). The phosphorylation reaction was terminated by heating the reaction to 70 degrees centigrade for 30 minutes. The cDNA was then digested with Xho 1 restriction enzyme (Stratagene) using standard molecular biology procedures. The cDNA was size fractionated into 12×100 uL fractions by passing it through a 1 mL (flat bed volume) column (Chroma Spin-400 from Clontech) using 1×STE (100 mM NaCl, 20 mM tris(hydroxymethyl)aminomethane-HCL (pH 7.5), 10 mM EDTA) (Stratagene) as the column buffer. 5 μL of each fraction was then visualised on an ethidium bromide-1.2% agarose tris(hydroxymethyl)aminomethane-borate-EDTA (TBE) electrophoresis gel (made in house using Sigma reagents). The first four fractions containing cDNA were then pooled, ethanol precipitated and resuspended in 10 μL 10 mM tris(hydroxymethyl)aminomethane (pH 7.6).

10 ng of the pooled cDNA were ligated into 20 ng pBluescript SK+Xho1/EcoR1 digested vector (Stratagene) in a 5

μL reaction at 12 degrees centigrade overnight using 2 units T4 DNA ligase in 1× ligation buffer+1 mM rATP. The cDNA library was then transformed into XL10-Gold ultracompetent cells (Stratagene) according to the manufacturer's instructions. The size of the primary cDNA library was estimated at 250,000 clones and the average insert size, 1072bP (base pairs). 2592 clones were hand picked and DNA prepared for sequencing.

Multiplication of cDNA for Sequencing

Colonies were grown up overnight in 2.5 mL of 2TY broth (16 g tryptone, 10 g NaCl, 10 g yeast extract (pH 7.3) per liter) (made in house using Sigma reagents) containing 100 μg/mL carbenicillin (Sigma) at 225 r.p.m. and 37° C. Plasmid DNA was isolated using montage plasmid miniprep (96) kit (Millipore) in accordance with the manufacturer's instructions. The DNA was then quantified and diluted to 50 ng/μL using PicoGreen DNA quantitation kit (Molecular Probes BV) in accordance with the manufacturer's instructions.

Sequencing of Expressed Sequence Tags, Compilation of Contigs and Identification of Homologues DNA sequencing was carried out on an Applied Biosystems Genetic Analyser 3100 using 5 μL of template DNA at 0.1 μg/μL and 1 μL of primer at 1 pmol/μL according to standard fluorescence dideoxy sequencing procedures. In total 1971 expressed sequence tag (EST) clones were sequenced and 1772 of these yielded good quality sequence data. These EST sequences were compiled into contigs. The consensus sequence of each of these contigs was used for identification of gene function by blasting against the following EMBL public databases 'plantdna', 'em_pl', 'emnew_pl', 'em_est_pl', 'em_gss_pl', 'em_nonpl', 'emnew_nonpl', 'em_est_nonpl' and 'em_gss_nonpl'. TblastX and blastN search programs were used and the ~500,000 results parsed into a database. A single (best annotated) homologue was identified for each of the tea genes (automated for single EST genes).

A single contig represented by 47 independent cDNA clones exhibited significant homology to AF220407, a *Vitis riparia* dehydrin-like protein (Dhn) mRNA (expectation score 3e-11). The tea dehydrin protein exhibited all the typical traits associated with a member of the dehydrin family. The sequence contained an N-terminal Y segment, an S segment, ϕ segments and two K segments near the C-terminal end as shown schematically and in actuality (SEQ. ID. 1) in FIGS. 3*a* and 3*b* respectively. No other single contig represented as many independent cDNA clones.

Cloning of Full Length and Truncated Tea Dehydrins into pDEST17 Expression Vector Full length wild type tea dehydrin protein and two truncated tea dehydrins were produced in accordance with the Gateway Expression System (Invitrogen) instructions. attB sequences (engineered foreign region from *Escherichia coli*) (Invitrogen) were added to either end of the dehydrin sequence from the cDNA vector (pBluescript from Invitrogen) in a two step polymerase chain reaction (PCR) process by using dehydrin template specific primers containing 12 attB nucleotides (Invitrogen) (see table 1). The specific primers were designed around full length and truncated tea dehydrin sequences to generate either full length or truncated DNA. The second step added the Universal attB sequence (Invitrogen) to the full length or truncated tea dehydrin sequence allowing it to be inserted into the pDONR221 vector (Invitrogen). The pDONR221 vector was then recombined with pDEST17 bacterial expression vector (with T7 promoter and ribosome binding site) (Invitrogen) which codes for the histidine residues to be added to the dehydrin allowing for purification of the protein.

Figures 5A, 5B:
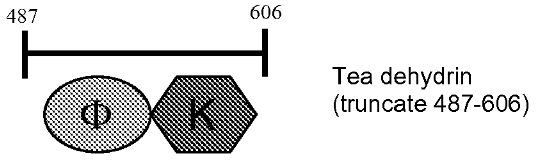
FIG. 5 shows the tea dehydrin of FIG. 3 in truncated form (truncate 163-201 of SEQ ID NO:1) in schematic form in FIG. 5*a* and in the form of a nucleotide and deduced amino acid sequence in FIG. 5*b* (SEQ ID NO:3)
Figure 8:
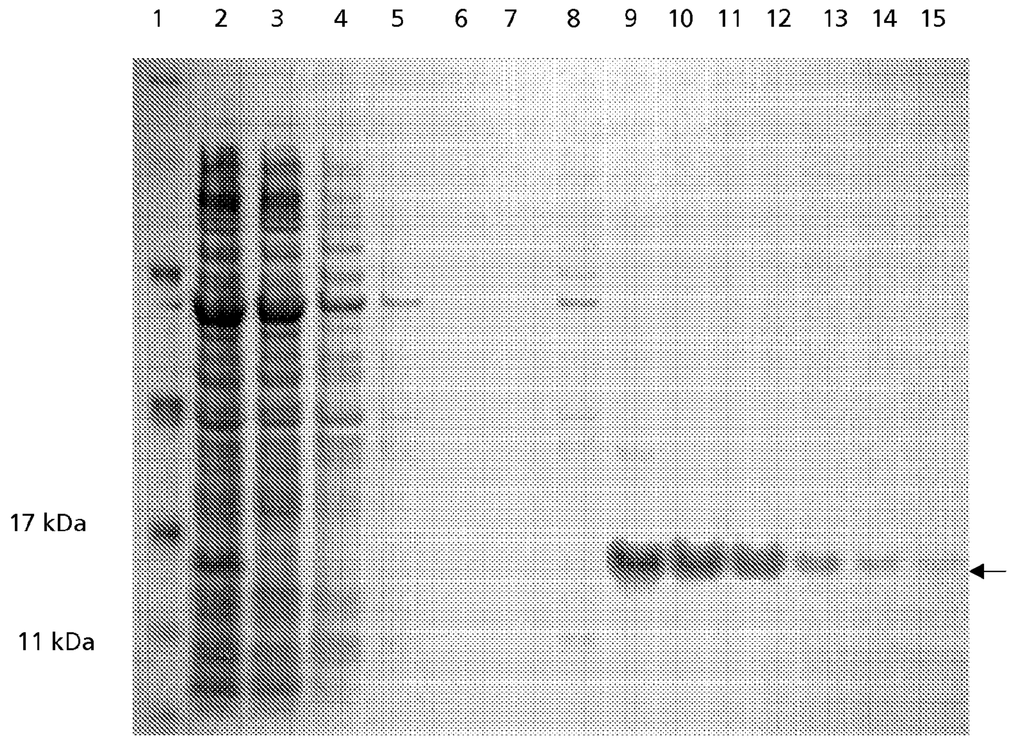
FIG. 8 shows SDS-PAGE gel plate of recombinant tea dehydrin (364-606) wherein the arrow indicates the position of the dehydrin fusion protein band, column (1) the molecular weight markers (kiloDaltons), column (2) the cell lysate supernatant of IPTG induced *E. coli* harbouring the pDEST 17-dehydrin construct, column (3) unbound proteins eluted from the Ni-NTA column after sample addition, columns (4) to (8) the contaminant proteins eluted after successive column washes, and columns (9) to (15) the fractions collected following Elution Buffer application.
Figure 9:
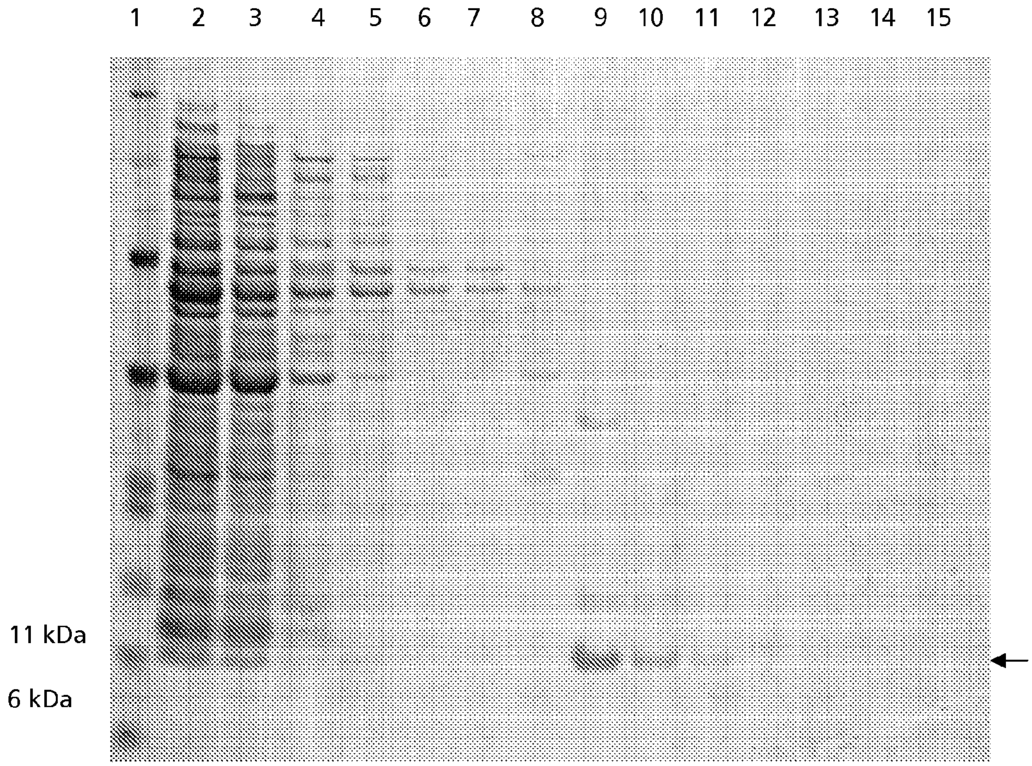
FIG. 9 shows SDS-PAGE gel plate of recombinant tea dehydrin (487-606) wherein the arrow indicates the position of the dehydrin fusion protein band, column (1) the molecular weight markers (kiloDaltons), column (2) the cell lysate supernatant of IPTG induced *E. coli* harbouring the pDEST 17-dehydrin construct, column (3) unbound proteins eluted from the Ni-NTA column after sample addition, columns (4) to (8) the contaminant proteins eluted after successive column washes, and columns (9) to (15) the fractions collected following Elution Buffer application.
Figure 10:
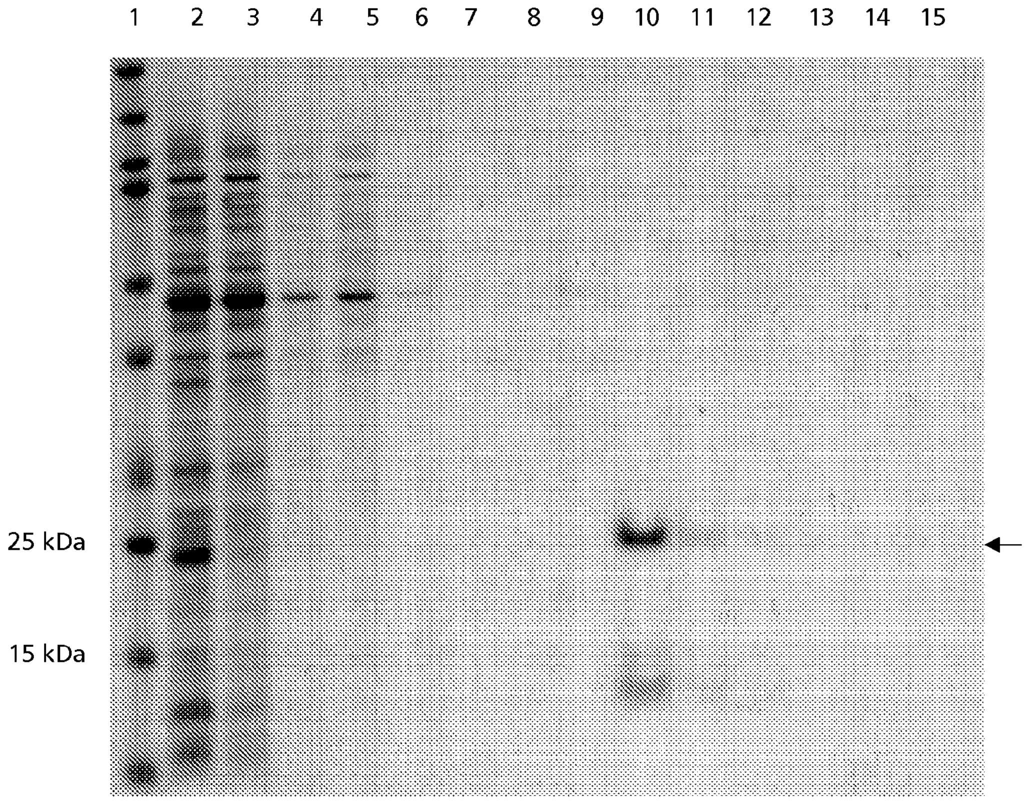
FIG. 10 shows SDS-PAGE gel plate of recombinant *Forsythia* dehydrin wherein the arrow indicates the position of the dehydrin fusion protein band, column (1) the molecular weight markers (kiloDaltons), column (2) the cell lysate supernatant of IPTG induced *E. coli* harbouring the pDEST 17-dehydrin construct, column (3) unbound proteins eluted from the Ni-NTA column after sample addition, columns (4) to (8) the contaminant proteins eluted after successive column washes, and columns (9) to (15) the fractions collected following Elution Buffer application.

Tea dehydrin truncate (deoxynucleotide numbers 364-606) was designed to encompass the C-terminal ϕ and the two K segments of the protein. The highly conserved K segment domain is believed to be vital for dehydrin activity. The smaller tea dehydrin truncate (deoxynucleotide numbers 487-606) was comprised of the C-terminal ϕ and one K segment only. FIGS. 4*a* and 5*a* show respectively the schematic nucleotide sequence of each tea dehydrin truncate and FIGS. 4*b* and 5*b* the actual nucleotide and deduced amino acid sequences of each tea dehydrin truncate (SEQ ID NO:2 and SEQ ID NO:3 respectively).

Isolation and Cloning of *Forsythia Suspensa* Dehydrin cDNA into pDEST17

In addition to the tea dehydrin, another dehydrin gene was isolated by real time polymerase chain reaction (RT-PCR) on polyadenylated RNA isolated from *Forsythia suspensa* bark. The lack of N-terminal *Forsythia* sequence meant that an alternative strategy was required to clone the *Forsythia* dehydrin. From amino acid sequence data, a short peptide TD/EEYGNPVQH (SEQ ID NO:18) with homology to dehydrins was identified. The presence of this short sequence together with data in the literature, for example conserved amino acid sequences of angiosperm dehydrins disclosed in table 1 of Close (Physiologica Plantarum, 100, 291-296 (1997)), offered an alternative approach to clone the *Forsythia* dehydrin. To achieve this goal two degenerate forward primers (FOR-D4 and FOR-D5) were designed to the 'Y-segment' dehydrin domain T/VDEYGNP (SEQ ID NO:19) (see FIG. 1) in accordance with Close (Physiologica Plantarum, 100, 291-296 (1997)). These would account for variation in the residues of the N-terminal consensus region between a threonine and valine. Therefore the primer FOR-D4 (ACIGAYGARTAYGGIAAYCC) (SEQ ID NO:5) utilised threonine as the first amino acid, whilst FOR-D5 (GTIGAYGARTAYGGIAAYCC) (SEQ ID NO:6) utilised valine as the first amino acid. The antisense primer FOR-R2 (ARYTTYTCYTTDATYTTRTCCAT) (SEQ ID NO:7) was designed to the 'K-segment' domain (EKKGIMDKIKEKLPG (SEQ ID NO:20)) (see FIG. 1) in accordance with Close (Physiologica Plantarum, 100, 291-296 (1997)). In the aforementioned primer sequences, the letter "I" represents inosine (which bonds with any base) and has been replaced, in the attached formatted sequence listings, with "N" which leads to the same technical effect as inosine. These primers were then used to synthesise the *Forsythia* dehydrin cDNA sequence using total polyadenylated RNA extracted from *Forsythia* bark as the template by RT-PCR. Primers were then designed to capture the 3' and 5' ends of the *Forsythia* cDNA using the GIBCO 5' RACE (Rapid Amplification of cDNA Ends) system kit version 2.0 (Life Technologies).

*Forsythia* cDNA was inserted into a vector pGEM®-T Easy vector from Promega) and cloned into pDEST17 as described above, using the Gateway Expression System (Invitrogen). FIG. 6 shows the *Forsythia* nucleotide and deduced amino acid sequences. Table 1 shows the primers used to clone the *Forsythia* dehydrin sequence into pDEST17.

TABLE 1

| Polymerase chain reaction (PCR) primers used to generate attB (engineered foreign region from *E. coli*) recombination target site flanked dehydrin sequences | | |
|---|---|---|
| Primer | Sequence 5' to 3' | Sequence Generated |
| 12attB1 TD (SEQ ID NO: 8) | AAAAAGCAGGCTTCATGGCACATAACAGCAAC | Full length tea dehydrin |
| 12attB2 TD* (SEQ ID NO: 9) | AGAAAGCTGGGTTTTATTTATTAGTGGTGGTGTG | |
| 12attB1 TD (364-606) (SEQ ID NO: 10) | AAAAAGCAGGCTTCATGGAGGATGATGGTCAAG | Truncated tea dehydrin |
| 12attB1 TD (487-606) (SEQ ID NO: 11) | AAAAAGCAGGCTTCATGGCAGCCACCACCGGT | Truncated tea dehydrin |
| 12attB1 FOR (SEQ ID NO: 12) | AAAAAGCAGGCTTCCTGCACTACTGAACAAACTTAG | *Forsythia* dehydrin |
| 12attB2 FOR (SEQ ID NO: 13) | AGAAAGCTGGGTTCATAAACTCGACTCAGACGCATG | *Forsythia* dehydrin |

*12attB2 TD also was used as the reverse primer for tea dehydrin (364-606) and tea dehydrin (487-606)

Expression in *E. Coli* and Purification of Recombinant Dehydrin Proteins

The pDEST 17 bacterial expression vector adds six consecutive histidine residues to the C-terminal end of the expressed protein. The histidine tag allowed rapid isolation of the protein from the soluble fraction of cell lysates by passage through a histidine tag binding nickel-affinity matrix (Ni-NTA from Pro-Bond Purification System from Invitrogen). Histidine fusion proteins expressed in pDEST 17 were purified from *E. coli* using the Pro-Bond Purification System (Invitrogen). Further details are provided below.

a) Cell Culture and Protein Expression pDEST 17 carrying the various dehydrin sequences was transformed into *E. coli* strain BL21 Star (DE3) One Shot (Invitrogen) (chemically competent BL21 hosts designed for improving protein yield in a T7 promoter-based expression system). Cells harbouring the pDEST 17 dehydrin constructs were spread onto lysogeny broth (LB) agar plates containing 100 μg/mL ampicillin and incubated at 37 degrees centigrade overnight. 2.5 mL of LB medium containing 100 μg/mL ampicillin was inoculated with a single colony of these cells and shaken at 37 degrees centigrade overnight. The 2.5 mL culture was used to inoculate 50 mL LB medium containing 100 μg/mL ampicillin and shaken at 37 degrees centigrade until the $A_{600}$ (absorbance at 600 nm) of the culture was 0.6. Dehydrin protein expression was then induced by the addition of isopropyl β-D-1-thiogalactopyranoside (IPTG) to a final concentration of 0.5 mM. Growth was continued for a further 5 hours under the same conditions. The cells were harvested by centrifugation at 10,000 rpm for 10 minutes and stored at −20 degrees centigrade until required.

b) Cell Lysis

Cell pellets were vigorously resuspended in 8 mL Binding Buffer (50 mM NaPO4, 0.5 M NaCl, 10 mM Imidazole pH 8.0). The protease inhibitor benzamidine was added to a final concentration of 1 mg/mL. Lysis was carried out by five successive cycles of flash freezing in liquid nitrogen followed by rapid thawing in a 30 degrees centigrade water bath. Deoxyribonuclease I (DNase I (a non-specific endonuclease that degrades double- and single-stranded DNA and chromatin)) was added to a final concentration of 1 ug/mL and the lysate incubated on ice for 30 minutes. Insoluble material was pelleted by centrifugation at 10,000 rpm for 1 hour at 4 degrees centigrade.

c) Protein Purification and Analysis

The 8 mL *E. coli* lysate supernatant was added to 2 mL of nickel ion-nitrolotriacetic acid resin (Ni-NTA) which had been pre-equilibrated with Binding Buffer. The mixture was incubated with mild agitation for one hour at room temperature to allow binding of the histidine tagged protein. Unbound material in the soluble fraction was removed by centrifuging the slurry at 800 g (800 times the force of gravity) for one minute and decanting the supernatant. Further contaminants were removed with five consecutive applications of Wash Buffer (50 mM NaPO4, 0.5 M NaCl, 100 mM imidazole). The histidine tagged protein was eluted from the resin by the addition of 8 mL of Elution Buffer (50 mM NaPO4, 0.5 M NaCl, 250 mM imidazole). Fractions were collected in 1 mL aliquots and analysed by SDS-PAGE gel electrophoresis (FIGS. 7 to 10). SDS-PAGE gel electrophoresis was carried out using the NuPAGE electrophoresis system (Invitrogen Ltd). Dehydrin protein containing fractions were pooled accordingly. Relative protein concentration was calculated using a Bradford Protein Assay (Bio-Rad).

Example 3

Expression in *Pichia Pastoris* and Purification of Recombinant Dehydrin Protein Expression of the full length tea dehydrin in *Pichia Pastoris* and subsequent purification was conducted by Invitrogen Corporation (1600 Faraday Avenue, Carlsbad, Calif. 92008, USA) as a fully-funded toll manufacture of the protein.

Example 4

Effects of Dehydrin Infusion

Observations of Rehydrated Tissue

Red pepper (*Capsicum*) pieces (1 $cm^3$) were prepared and fully immersed in 0.1 mg/mL dehydrin solution (*Selaginella lepidophylla* dehydrin obtained from example 1 or tea dehydrin expressed from *Pichia Pastoris* as obtained from example 3) and vacuum infused for two hours at room temperature. Water infused pieces were also prepared as controls. The infused plant tissue was dried for six hours at 60 degrees centigrade and rehydration carried out by immersion in water overnight at room temperature.

Figure 11:
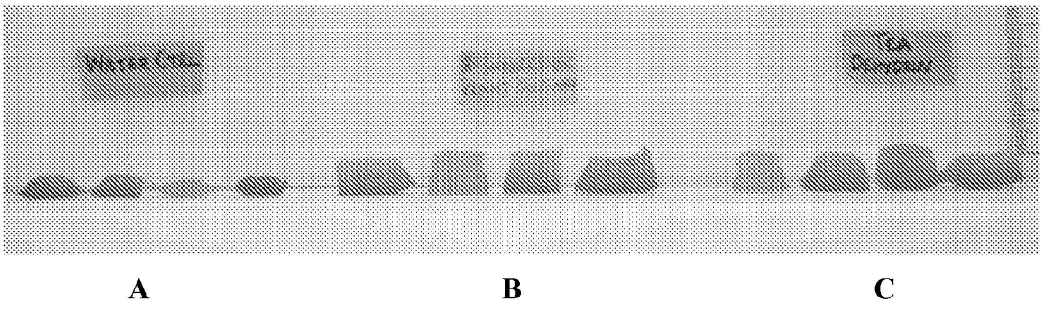
FIG. 11 shows fully dried and rehydrated red peppers following infusion (A) with water, (B) *Selaginella lepidophylla* dehydrin, and (C) tea dehydrin expressed from *Pichia pastoris;*

FIG. 11 illustrates the greater rehydration of the red pepper pieces that were infused with dehydrin, both that originating from *Selaginella lepidophylla* (B) and tea dehydrin expressed from *Pichia Pastoris* (C) compared to the water-infused control (A).

Example 5

Effects of Dehydrin Infusion

Dimensions of Rehydrated Tissue

Figure 12:
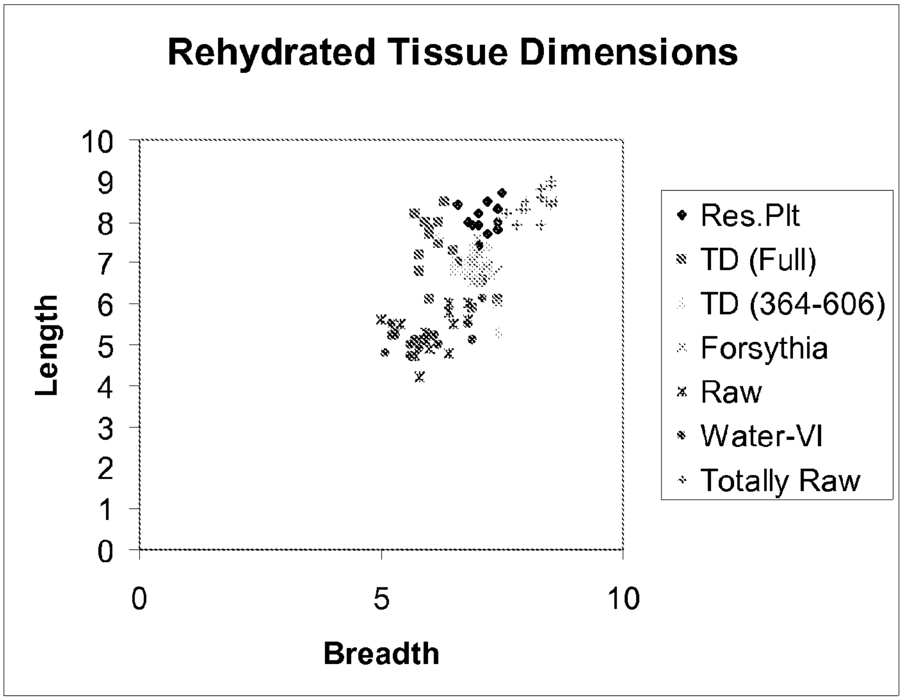
FIG. 12 shows a graph of the length versus breadth of rehydrated red pepper tissue pieces infused with various dehydrins or water and controls, wherein “Res Plt” refers to the *Selaginella lepidophylla* dehydrin of example 1, “TD” refers to the full tea dehydrin of example 2, “TD (364-606)” refers to a truncated tea dehydrin of example 2, “*Forsythia*” refers to the *Forsythia* dehydrin of example 2, “Raw” refers to raw red pepper tissue pieces which have been dried and rehydrated in accordance with example 5, “Water-VI” refers to raw red pepper tissue pieces which have been vacuum infused with water, dried and then rehydrated in accordance with example 5, and “Totally raw” refers to raw red pepper tissue pieces.

To assess the effect of different dehydrins on red pepper (*Capsicum*) tissue dimensions, post-rehydration, pieces of red pepper were vacuum infiltrated with aqueous dehydrin solution at 0.5 mg/mL or water alone for four hours at room temperature, dried for 16 hours at 37 degrees centigrade, and rehydrated in water at room temperature for 4 to 5 hours. Typically 10 to 15 pieces of plant tissue, prepared by using a circular 1 cm diameter cork borer, were used for each dehydrin. As a control, raw red pepper tissue pieces were also dried and rehydrated in accordance with this example. The length and breadth of rehydrated samples are shown in FIG. 12 wherein "Res Plt" refers to the *Selaginella lepidophylla* dehydrin of example 1, "TD" refers to the full tea dehydrin of example 2, "TD (364-606)" refers to a truncated tea dehydrin of example 2, "*Forsythia*" refers to the *Forsythia* dehydrin of example 2, "Raw" refers to raw red pepper tissue pieces which have been dried and rehydrated in accordance with this example, "Water-VI" refers to raw red pepper tissue pieces which have been vacuum infused with water, dried and then rehydrated in accordance with this example, and "Totally raw" refers to raw red pepper tissue pieces.

The measured dimensions of rehydrated tissue indicated greater rehydration of dehydrin infused tissue compared to controls with no dehydrin infusion. In fact the dehydrin infused tissue dimensions are closer to the dimensions of fresh pieces with no infusion, drying or rehydration treatment.

Example 6

Effects of Dehydrin Infusion

Figure 13A:
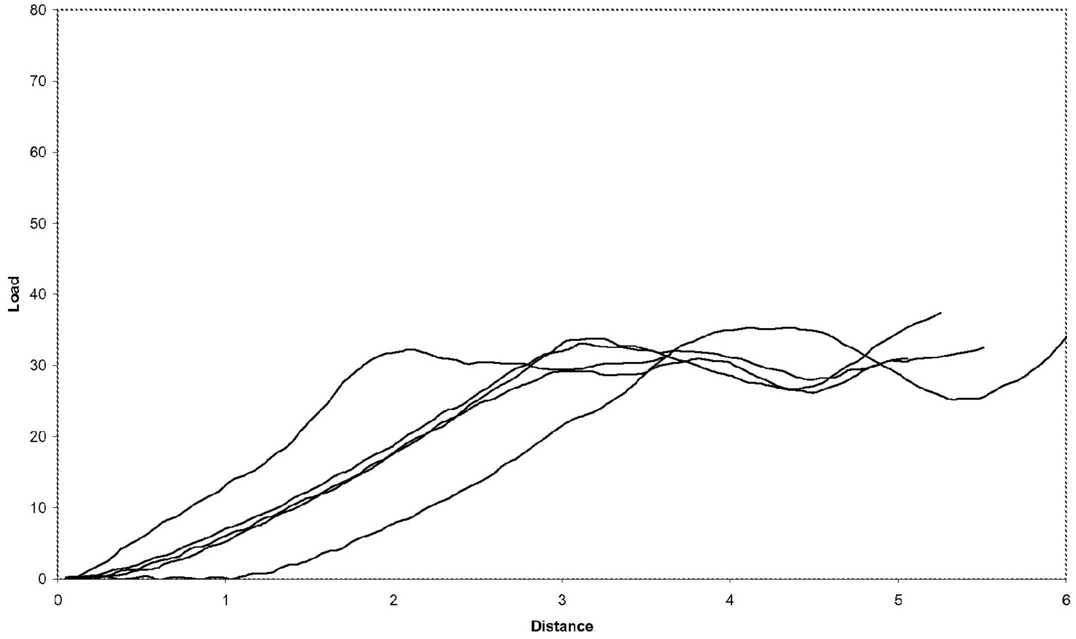
FIG. 13 shows load (N) versus distance (mm) graphs for pieces of green pepper (*Capsicum*) which have not been infused, dried and rehydrated (FIG. 13*a*), which have not been infused but nevertheless dried and rehydrated in accordance with this example 6 (FIG. 13*b*), which have been infused with water, dried and rehydrated in accordance with example 6 (FIG. 13*c*); and which have been infused with *Selaginella lepidophylla* dehydrin, dried and rehydrated in accordance with example 6 (FIG. 13*d*)
Figure 13B:
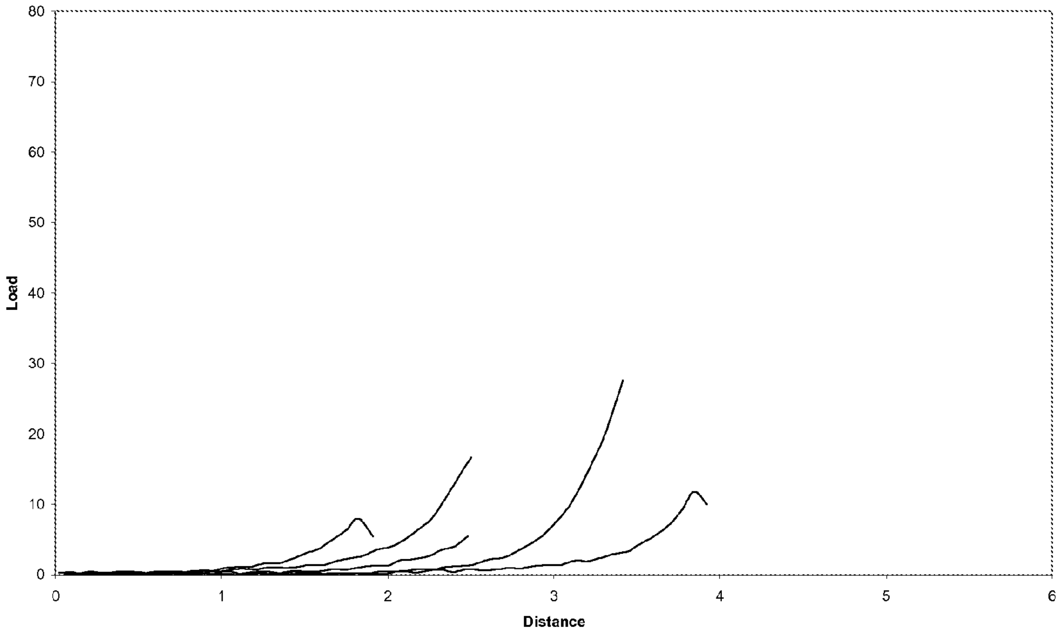
Figure 13C:
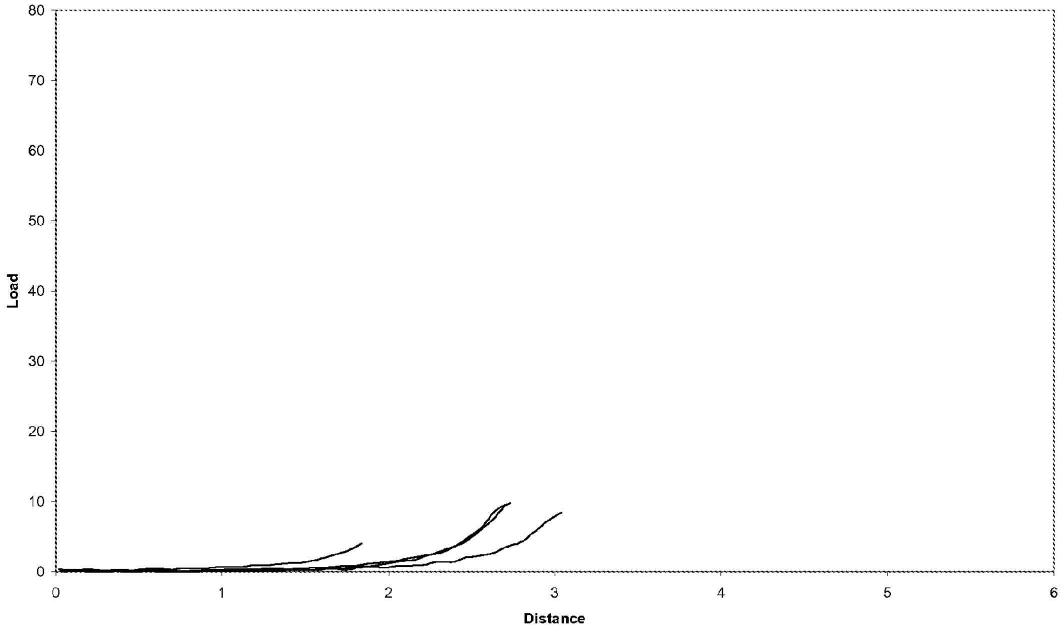
Figure 13D:
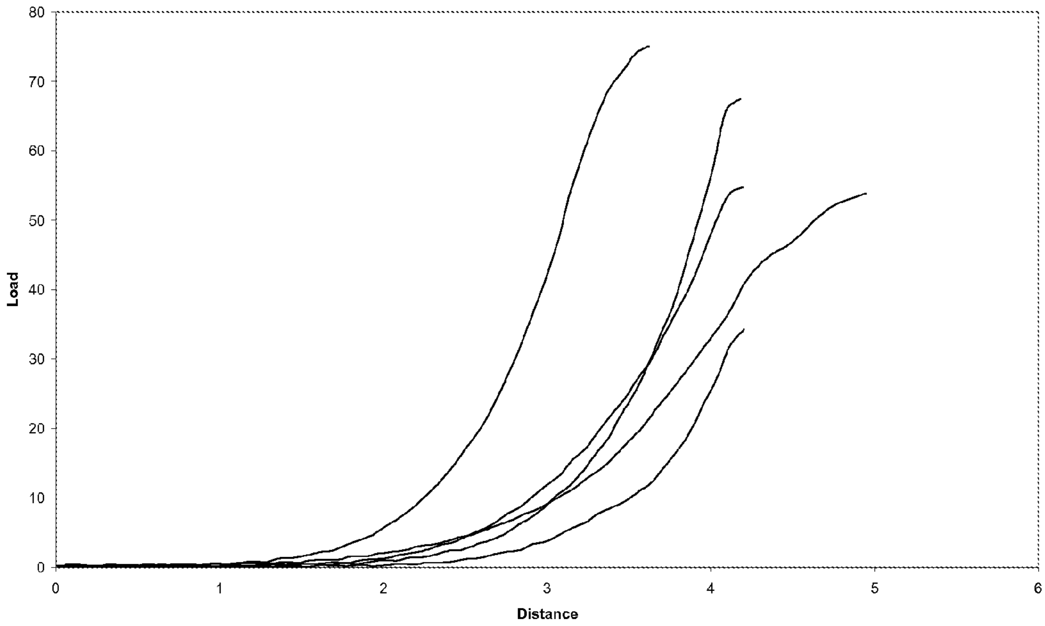

Mechanical Properties of Rehydrated Tissue 10 to 15 pieces of green pepper (*Capsicum*), prepared by using a circular 1 cm diameter cork borer, were vacuum infused (overnight at room temperature) with either *Selaginella lepidophylla* dehydrin of example 1 in the form of an aqueous solution of 0.05 mg/mL or water. The infused pieces of green pepper were then dried at 45 degrees centigrade for 7.5 hours and rehydrated (3 hours at room temperature). The rehydrated pieces were then subjected to compression tests using a Dartec Servohydraulic Mechanical Testing machine to assess their mechanical properties. Specifically the pieces were compressed to a height of 2 mm at a crosshead speed of 40 mm/sec and the load (N) in order to do this was measured. The results for the two infused (FIG. 13*c* for water infused pieces and FIG. 13*d* for *Selaginella lepidophylla* dehydrin infused pieces) variants are shown in FIG. 13 together with controls for raw green pepper pieces which have not been infused but nevertheless dried and rehydrated in accordance with this example (FIG. 13*b*), and raw green pepper tissue pieces which have not been infused, dried and rehydrated (FIG. 13*a*).

Rehydrated *Selaginella lepidophylla* dehydrin-infused pieces required a greater force during compression compared with non-infused and water-infused controls. This indicates that the rehydrated dehydrin infused pieces were firmer than the rehydrated controls. Infusion with the dehydrin gave results closest to those from raw green pepper pieces which have not been infused, dried and rehydrated.

Example 7

Effects of Dehydrin Infusion

Observations of Leaf Tissue

Spinach leaves were immersed in a 0.2 mg/mL aqueous solution of *Pichia Pastoris* expressed tea dehydrin in accordance with example 3, along with a water control, then both vacuum infused for three hours at room temperature. The infused leaves were dehydrated at 40 degrees centigrade overnight and then rehydrated for up to 3 hours at room temperature.

Figure 14:
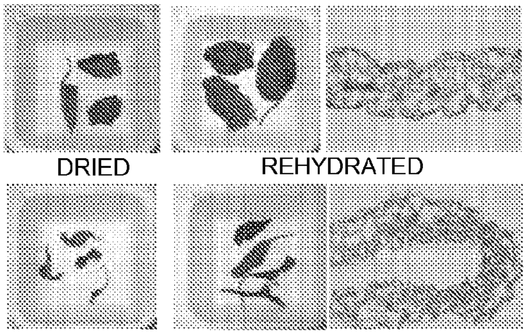
FIG. 14 shows spinach leaves infused with *Pichia pastoris* expressed tea dehydrin (upper images) or water (lower images) after being dried (left hand images) and then rehydrated (middle images), and optical microscopy of a section of one of the leaves shown in the middle images (right hand images)

Images of the dried (left hand images) and rehydrated leaves (middle images) are shown in FIG. 14 along with optical microscope images of the internal structure of the rehydrated tissues (right hand images). It can be observed that the dehydrin infused spinach (upper images) had a larger leaf, after being both dried and rehydrated, compared to the water infused control (lower images), and a more open, less collapsed tissue structure upon rehydration. This indicated greater rehydration of the dehydrin infused leaves.

Example 8

Detection and Quantification of Dehydrin in Dry Plant Material a) Extraction and Estimation of Dehydrin Found Naturally in Red Pepper Red pepper pericarp were oven-dried at 60 degrees centigrade until constant weight, weighed, ground in a mortar under liquid nitrogen, and the ground material placed in a 2 mL Eppendorf tube, extracted with Tissue Extraction Reagent 1 (Invitrogen) (containing 50 mM tris(hydroxymethyl)aminomethane, pH7.4, 250 mM NaCl, 5 mM EDTA, 2 mM $Na_3VO_4$, 1 mM NaF, 20 mM $Na_4P_2O_7$, 0.02% $NaN_3$, detergent and 0.5 mM phenylmethylsulfonyl fluoride) in a 1 mL extraction per 100 mg of ground material by shaking for 1 hour at 4 degrees centigrade and centrifuging at 14,000 rpm, and the supernatant flash frozen and stored at −80 degrees centigrade. Total proteins were quantified using the Bradford Protein Assay (Bio-Rad).

10 μL of the protein extract was loaded onto a 4-12% bis-(2-hydroxy-ethyl)-amino-tris(hydroxymethyl)-methane SDS-PAGE gel. 10 μL of the tea dehydrin of example 3 were prepared at concentrations of 0.5, 0.1 and 0.05 mg/mL and loaded onto the gel. The gel was run at 200 V for 30 minutes to separate the proteins. Protein standards (All Blue Precision Plus Protein Standards (Bio-Rad)) were also run alongside the aforementioned sample.

The proteins were transferred from the SDS-PAGE gel onto a 0.2 μm polyvinylidene fluoride (PVDF) membrane (Invitrogen) in a semi dry blotting module. The PVDF membrane was then rinsed and dried between filter paper. The dry membrane with transferred proteins was then incubated in blocking buffer (phosphate buffered saline (PBS) solution with Polysorbate 20 (Tween 20) for use as a wash buffer and diluent (PBST)+4% skimmed milk powder (SMP) solution, pH 7.2), for 30 minutes and then removed. The membrane was then incubated for 2 hours with rabbit anti-dehydrin polyclonal antibody (Agrisera, Vannas, Sweden) at a dilution of 1:1000 in PBST+SMP. After 6 consecutive 4 minute washes in PBST, the membrane was incubated for 1 hour with peroxidase-conjugated affinipure donkey anti-rabbit immunoglobulin G secondary antibodies (Jackson ImmunoResearch Laboratories, Baltimore, Md.) at a dilution of 1:5000 in PBST+SMP. After incubation the membrane was washed 6×4 minutes, then drained and developed using a chemiluminescent substrate (such as a Super Signal West Pico chemiluminescent substrate) and imaged in a ChemiDoc-XRS (chemiluminescence) Imaging System (Bio-Rad).

Intensity of the red pepper dehydrin bands on the membrane were compared to those of the concentration gradient of the dehydrin standards and relative concentrations of red pepper dehydrin in red pepper estimated by eye and back calculated to amounts present per gram of dry red pepper core. The results indicated that natural levels of dehydrin in red pepper vary from non-detectable to approximately 20% of that of the lowest dehydrin standard concentration, that is to say about 0.01 mg/mL equivalent to 0.1 mg dehydrin per g dry weight, or 0.01% w/w.

b) Infusion of Red Pepper with Exogenous Dehydrin and Estimation of Levels Thereof Red pepper pericarp was cored using a circular 1 cm diameter cork borer, the pieces rinsed in water and blotted dry on tissue paper. A 1 mg/mL aqueous solution of the tea dehydrin of example 3 was prepared and 2 mL of the solution used to cover 3 pepper cores in a 10 mL beaker. These pieces were then vacuum infused for 4 hours at room temperature. After infusion the pieces were rinsed three times in water to remove surface dehydrin and blotted dry on tissue paper. The infused pieces were then placed in an air assisted fan oven to dry until constant weight, starting at 40 degrees centigrade for 1 hour followed by 60 degrees centigrade for 5 hours. Protein was extracted from the pieces as described above.

2 μL of the total protein extract was loaded onto two a 4-12% bis-(2-hydroxy-ethyl)-amino-tris(hydroxymethyl)-methane SDS-PAGE gel. An extract from a non-infused red pepper was loaded as a control. 10 μL of three standards of pure dehydrin (Invitrogen) were loaded alongside at different concentrations (0.5, 0.1 and 0.05 mg/ml). Molecular markers (All Blue Precision Plus Protein Standards from Bio-Rad) were also run. The gel was run at 200 V for 30 minutes to separate proteins by effective molecular weight. Proteins from one gel were transferred to a PVDF membrane and probed with anti-dehydrin antibody using Western Blotting as described above to confirm proteins observed in infused tissue extracts at ~37 kDa were dehydrin proteins. The other gel was stained for 1 hour (with Simply Blue Safe Stain from Invitrogen) and then destained overnight before imaging. Proteins on the dye stained SDS-PAGE gel were imaged using a gel imaging system (Gel Logic 200 imaging system from Gel Logic) and the images adjusted using brightness, contrast and inversion to remove background and highlight areas of intense protein concentration to allow an estimation of the amount of dehydrin infused into red pepper tissue. Estimation of concentration of dehydrin on the gel was back calculated to estimate amounts present per gram of dry red pepper tissue.

The infused red pepper extract showed an intense protein band at ~37 kDa, equivalent in size to that of the pure dehydrin infused into the tissue and used for the concentration gradient, this band was absent from the non-infused control. The intensity of the band was between that of 1 and 5 μg of pure dehydrin standard loaded onto the gel and thus more than 1 μg, but less than 5 μg per 2 μL of extract. As the extract was 10 mL/gram dry tissue, the amount of dehydrin infused was about 5 mg dehydrin per g of dry tissue, but not more than 25 mg/g (0.5-2.5% dehydrin per dry weight).

Example 9

Effects of Dehydrin Infusion on Onion Monolayer

Onion (*Allium cepa*) epidermal peels were used as a model plant cell monolayer system. Epidermal cells (1 cm×2 cm) were prepared and fully immersed in 0.1 mg/mL full-length *Camellia sinensis* dehydrin (obtained from example 2) solution in 50 mM Bis-Tris buffer with 0.25 M trehalose (BTT buffer). The dehydrin was vacuum infused into onion tissue for two hours at room temperature. Water, 0.1 mg/mL bovine serum albuinin (BSA) in BTT buffer and BTT buffer only infused peels were also prepared as controls. 0.75 g of infused onion tissue was dried overnight at 50 degrees centigrade and rehydration carried out by immersion in 25 mL water for 2 hours at room temperature.

Rehydrated tissues were mounted on microscope slides and stained in-situ with 0.04% (w/v) trypan blue. After rinsing with deionised water, cover slips were applied and slides were observed with a light microscope (Leica DMRB) at 10× magnification. A digital colour camera (JVC KY-F75U) was used to capture images (JVC KY-LINK Software).

Figure 15A:
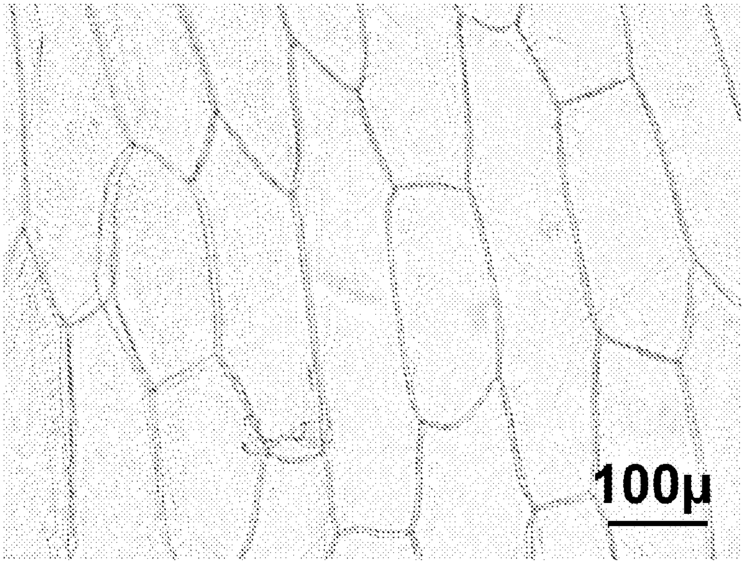
FIG. 15 shows a visible light micrograph (×10 magnification) of in (a) of live onion epidermal peel dyed with trypan blue and in (b) onion epidermal peel which has been blanched and then dyed with trypan blue.
Figure 15B:
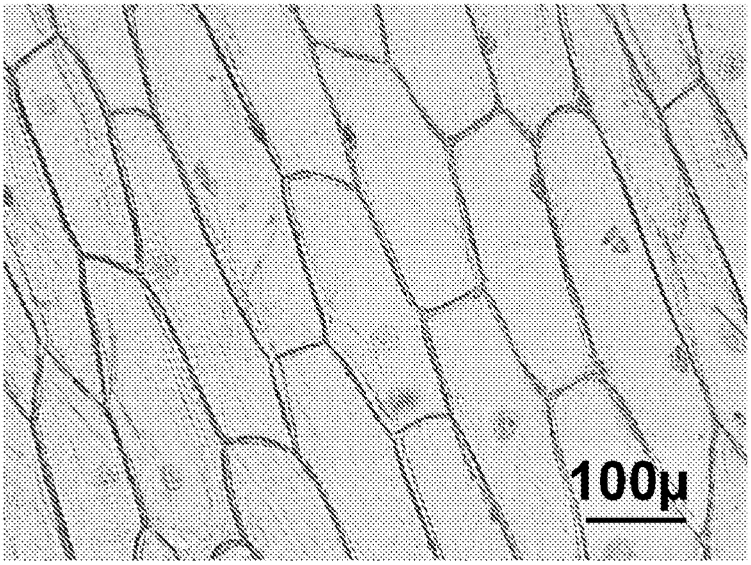

Trypan blue is a vital dye used for visualising cell viability. FIG. 15*a* shows live cells or tissues with intact cell membranes which exclude the dye as highlighted in the fresh tissue control samples. The dye can enter cells with damaged cell membranes, for example in blanched tissue (blanched 2 minutes, boiling water) making the nuclei clearly visible and the membranes appear to detach from the cell walls as shown in FIG. 15*b*.

Figure 16A:
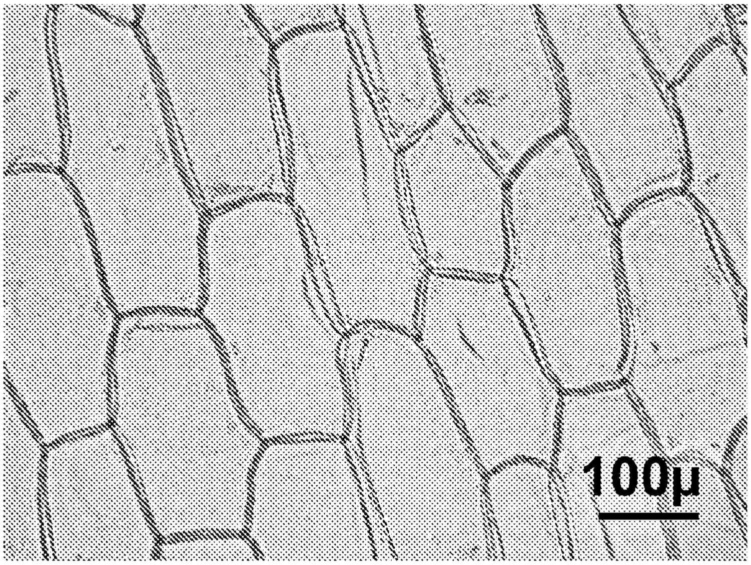
FIG. 16 shows visible light micrographs (×10 magnification) of dried and rehydrated onion epidermal peels stained with the uptake of trypan blue following infusion with (a) the full-length tea dehydrin of example 2, (b) deionised water, (c) bis-tris trehalose buffer, and (d) BSA in bis-tris trehalose buffer.
Figure 16B:
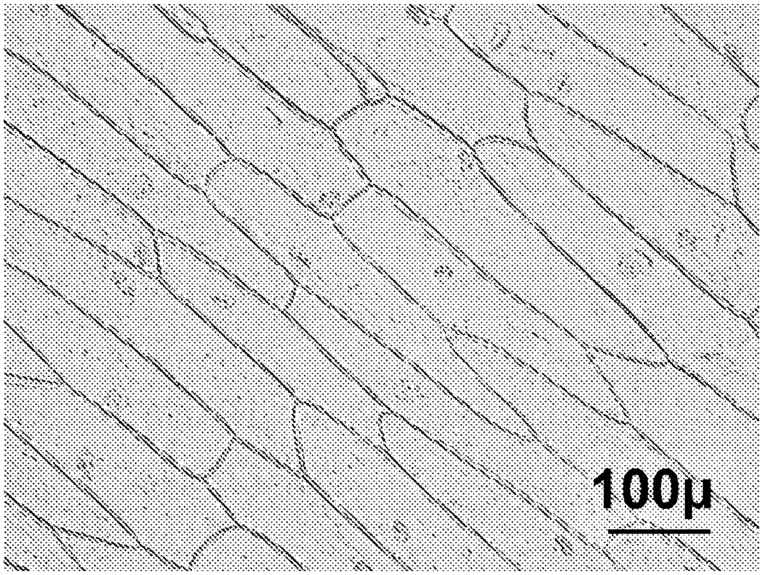
Figure 16C:
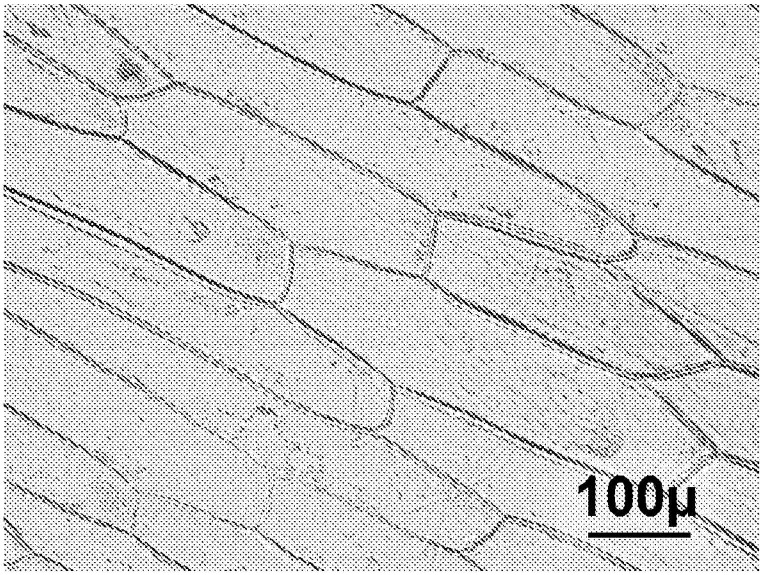
Figure 16D:
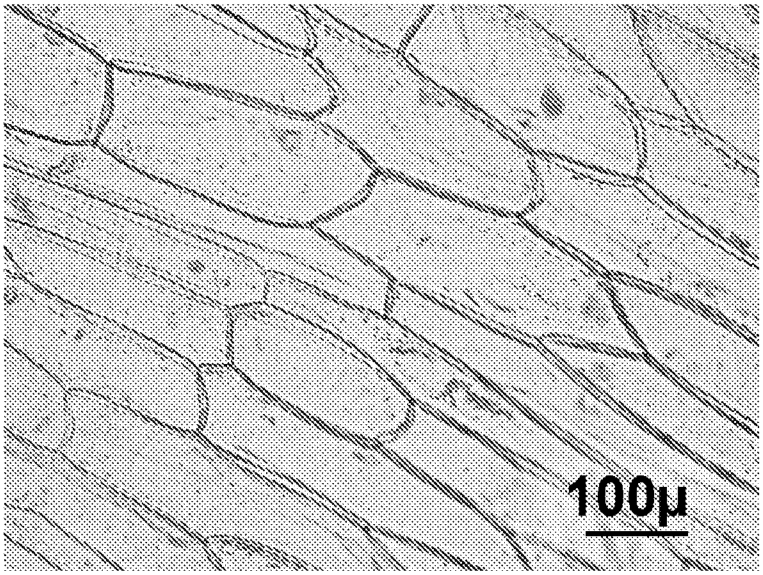

FIG. 16*a* shows that dehydrin infused onion epidermal peel following drying and rehydration showed little evidence of tissue damage and the cell nuclei are not visible. The cells also appeared swollen compared to the controls with no dehydrin (FIGS. 16*b-d*), indicating greater rehydration. In particular, the controls with no dehydrin showed signs of tissue damage and the nuclei are visible. The extent of cell swelling in the water (FIG. 16*b*) and buffer (FIG. 16*c*) controls was lower than the dehydrin infused sample indicating a limited uptake of water on rehydration.

The swelling of the BSA infused control (FIG. 16*d*) was intermediate between dehydrin infused tissue (FIG. 16*a*) and water/buffer controls (FIGS. 16*b* and *c*) indicating retention of water inside cells. However the membranes were not protected and allowed the passage of vital dye inside the cells, evidenced by nuclear staining.

The invention claimed is:

1. A dried rehydratable food comprising less than 10% w/w water and at least 0.02% w/w of a dehydrin protein, a glycosilated dehydrin or a truncated dehydrin derived from the dehydrin protein, said dehydrin protein, glycosylated dehydrin or truncated dehydrin having a molecular weight of 1 to 150 kD and comprising an amino acid sequence selected from the group consisting of KIKEKLPG (SEQ ID No: 14); KIKE/DKL/IPG (SEQ ID No: 15); and KIKE/DKL/I/T/VP/H/SG (SEQ ID No: 16), and wherein the dried rehydratable food is unbroken tissue of a vegetable or part thereof and/or a fruit or part thereof, and not a seed, wherein the unbroken tissue has a shortest linear dimension of at least 0.5 millimeters, and wherein the rehydratable food may be rehydrated to at least 50%, of the water content of a fully hydrated vegetable or part thereof and/or fruit or part thereof.

2. A dried rehydratable food according to claim 1, wherein the dehydrin protein, glycosilated dehydrin or truncated dehydrin has a molecular weight of 5 to 150 kD and wherein the rehydratable food may be rehydrated to at least 60%, of the water content of a fully hydrated vegetable or part thereof and/or fruit or part thereof.

3. A dried rehydratable food according to claim 1 comprising 0.02 to 20% w/w dehydrin protein, glycosylated dehydrin or truncated dehydrin.

4. A dried rehydratable food according to claim 1, wherein the dehydrin protein glycosylated dehydrin or truncated dehydrin have a molecular weight of 5 to 100 kD.

5. A dried rehydratable food according to claim 1, wherein the dehydrin protein glycosylated dehydrin or truncated dehydrin is a dehydrin derived from the group consisting of *Camellia sinensis, Forsythia* and *Selaginella.*

6. A dried rehydratable food according to claim 1, wherein the dehydrin protein, glycosylated dehydrin or truncated dehydrin has an amino acid sequence at least 80% identical to SEQ ID No: 1.

7. A dried rehydratable food according to claim 1, wherein the dehydrin protein, glycosylated dehydrin or truncated dehydrin has an amino acid sequence at least 80% identical to SEQ ID No: 2.

8. A dried rehydratable food according to claim 1, wherein the dehydrin protein, glycosylated dehydrin or truncated dehydrin has an amino acid sequence at least 80% identical to SEQ ID NO: 3.

9. A dried rehydratable food according to claim 1, wherein the rehydratable food additionally comprises a compound selected from the group consisting of trehalose, sucrose, glucose, fructose, raffinose, an enzymatic antioxidant or a non-enzymatic reactive oxygen species scavenger.

10. A dried rehydratable food according to claim 9, wherein the enzymatic antioxidant is selected from the group consisting of catalase, superoxide dismutase, ascorbate peroxidase and glutathione reductase.

11. A dried rehydratable food according to claim 9, wherein the non-enzymatic reactive oxygen species scavenger is selected from the group consisting of ascorbate, glutathione and a carotenoid.

12. A dried rehydratable food according to claim 1, wherein the vegetable is selected from the group consisting of spinach, broccoli, onion, aubergine, courgette, potato, pumpkin, mushroom, carrot, tea, asparagus, turnip, leek, beetroot, cauliflower, celeriac, artichoke, mint, thyme, oregano, rosemary, parsley, sage, chives, marjoram, basil, bay leaf, tarragon, celery and garlic and the fruit is selected from the group consisting of lemon, raspberry, red currant, blackberry, berry, blueberry, strawberry, pineapple, banana, peach, apricot, lychee, apple, pear, tomato, *capsicum*, cucumber and mango.

13. A food product comprising a dried rehydratable food according to claim 1.

14. A food product according to claim 13 which is selected from the group consisting of a dried soup, a dried beverage, a breakfast cereal, a yoghurt and a dried sauce.

15. A method for manufacturing a dried rehydratable food according to claim 1, the method comprising the steps of:

(a) Infusing a vegetable or part thereof, or a fruit or part thereof excluding a seed, with a dehydrin protein a glycosylated or a truncated dehydrin derived from the protein dehydrin, said dehydrin protein, glycosylated dehydrin or truncated dehydrin having a molecular weight of 1 to 150 kD and comprising an amino acid sequence selected from the group consisting of KIKEKLPG (SEQ ID NO:15); KIKE/DKL/IPG (SEQ ID NO:16); and KIKE/DKL/I/T/VP/H/SG (SEQ ID NO 17) to produce an infused food; and (b) Drying the infused food thereby to produce a dried rehydratable food according to claim 1.

16. A method for manufacturing a dried rehydratable food according to claim 15, wherein step (a) of claim 15 is carried out under a vacuum.

17. A method for manufacturing a dried rehydratable food according to claim 15, wherein step (a) of claim 15 is carried out at a temperature of 3 to 70 degrees centigrade.

18. A method for manufacturing a dried rehydratable food according to claim 1, the method comprising the steps of:

(a) Cloning a gene into a plant expression vector thereby to produce a modified plant expression vector, wherein the gene encodes a dehydrin protein and derivatives thereof, wherein the dehydrin protein and derivatives thereof comprises an amino acid sequence selected from the group consisting of KIKEKLPG (SEQ ID NO:14); KIKE/DKL/IPG (SEQ ID NO:15); and KIKE/DKL/I/T/VP/H/SG (SEQ ID NO:16);

(b) Introducing the modified plant expression vector into a target crop by plant transformation thereby to produce a transgenic target crop;

(c) Growing the transgenic target crop thereby to express the dehydrin protein and derivatives thereof; and then (d) Drying the transgenic target crop thereby to produce a dried rehydratable food according to claim 1.

* * * * *

SEQUENCE LISTING

<160> NUMBER OF SEQ ID NOS: 20

<210> SEQ ID NO 1
<211> LENGTH: 201
<212> TYPE: PRT
<213> ORGANISM: Camellia sinensis

<400> SEQUENCE: 1

Met Ala His Asn Ser Asn Gln Tyr Gly Asn Pro Pro Arg Gln Thr Asp
1               5                   10                  15

Glu Tyr Gly Asn Pro Pro Arg Lys Thr Asp Glu Phe Gly Asp Pro Val
            20                  25                  30

Arg Gln Ile Asp Glu Tyr Gly Asn Pro Val His His Thr Gly Thr Met
        35                  40                  45

Gly Asp Tyr Gly Thr Thr Thr Gly Thr Thr Gly Val His Gly Thr His
    50                  55                  60

Thr Gly Thr Thr Gly Thr Tyr Gly Thr Gly Thr Thr Gly Thr Tyr Gly
65                  70                  75                  80

Thr Gly Met Asp Thr Thr Gly Thr Thr Gly Thr His Gly Leu Ser Thr
                85                  90                  95

Gly Thr Gly Gly His His Gln Gln His Ala Asp Gly Gly Val Leu His
            100                 105                 110

Arg Ser Gly Ser Ser Ser Ser Ser Ser Glu Asp Asp Gly Gln Gly Gly
        115                 120                 125

Arg Arg Lys Lys Lys Gly Leu Thr Gln Lys Ile Lys Glu Lys Leu Pro
    130                 135                 140

Gly Gly His Lys Asp Gln Thr Pro Gln Tyr Asp Asn Thr Thr Thr Thr
145                 150                 155                 160

Pro Gly Ala Ala Thr Thr Gly Gly Tyr Gly Tyr Gly Gly Glu Asp Gln
                165                 170                 175

Gln Gln Tyr Pro Glu Lys Lys Gly Met Met Glu Lys Ile Lys Glu Lys
            180                 185                 190

Leu Pro Gly His Thr Thr Thr Asn Lys
        195                 200

<210> SEQ ID NO 2
<211> LENGTH: 80
<212> TYPE: PRT
<213> ORGANISM: Artificial
<220> FEATURE:
<223> OTHER INFORMATION: Truncate 122-201 of Seq ID 1

<400> SEQUENCE: 2

Glu Asp Asp Gly Gln Gly Gly Arg Arg Lys Lys Lys Gly Leu Thr Gln
1               5                   10                  15

Lys Ile Lys Glu Lys Leu Pro Gly Gly His Lys Asp Gln Thr Pro Gln
            20                  25                  30

Tyr Asp Asn Thr Thr Thr Thr Pro Gly Ala Ala Thr Thr Gly Gly Tyr
        35                  40                  45

Gly Tyr Gly Gly Glu Asp Gln Gln Gln Tyr Pro Glu Lys Lys Gly Met
    50                  55                  60

Met Glu Lys Ile Lys Glu Lys Leu Pro Gly His Thr Thr Thr Asn Lys
65                  70                  75                  80

<210> SEQ ID NO 3
<211> LENGTH: 39
<212> TYPE: PRT
<213> ORGANISM: Artificial

```
<220> FEATURE:
<223> OTHER INFORMATION: Truncate 163-201 of Seq ID 1

<400> SEQUENCE: 3

Ala Ala Thr Thr Gly Gly Tyr Gly Tyr Gly Gly Glu Asp Gln Gln Gln
1               5                   10                  15

Tyr Pro Glu Lys Lys Gly Met Met Glu Lys Ile Lys Glu Lys Leu Pro
            20                  25                  30

Gly His Thr Thr Thr Asn Lys
        35


<210> SEQ ID NO 4
<211> LENGTH: 128
<212> TYPE: PRT
<213> ORGANISM: Forsythia suspensa

<400> SEQUENCE: 4

Met Glu Gln Tyr Gly Asp Gln His Gly Asn Gln Ile Arg Lys Thr Asp
1               5                   10                  15

Glu Tyr Gly Asn Pro Val Gln His Thr Gly Lys Gln Gly Thr Gly Gln
            20                  25                  30

Gly Gly Ile Ala Pro Gly Thr Leu Asp Ala Gly Leu Ala Gly Gln Gln
        35                  40                  45

His Gly Gln Leu Arg Arg Ser Gly Ser Ser Ser Ser Glu Asp Asp Gly
    50                  55                  60

Leu Gly Gly Arg Arg Lys Lys Gly Met Lys Asp Lys Ile Lys Glu Lys
65                  70                  75                  80

Leu Pro Gly Gly His Lys Asp Glu Gln Asn Tyr Gly Thr Gln Thr Thr
                85                  90                  95

Thr Pro Ala Gly Gly Tyr Gly Cys Gly Gly Gly Glu His Gln Glu Lys
            100                 105                 110

Lys Gly Val Val Glu Lys Ile Lys Glu Lys Leu Pro Gly Gly Gly His
        115                 120                 125


<210> SEQ ID NO 5
<211> LENGTH: 20
<212> TYPE: DNA
<213> ORGANISM: Artificial
<220> FEATURE:
<223> OTHER INFORMATION: Primer for Forsythia DNA. 'i' denotes inosine
      and has been replaced by 'n' on positions 3 and 15.
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: modified_base
<222> LOCATION: (15)..(15)
<223> OTHER INFORMATION: I
<220> FEATURE:
<221> NAME/KEY: misc_feature
<222> LOCATION: (15)..(15)
<223> OTHER INFORMATION: n is a, c, g, or t

<400> SEQUENCE: 5

acngaygart ayggnaaycc                                                 20


<210> SEQ ID NO 6
<211> LENGTH: 20
<212> TYPE: DNA
```

-continued

```
<213> ORGANISM: Artificial
<220> FEATURE:
<223> OTHER INFORMATION: Primer for Forsythia DNA. 'i' denotes inosine
      and has been replaced by 'n' on positions 3 and 15.
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: modified_base
<222> LOCATION: (15)..(15)
<223> OTHER INFORMATION: I
<220> FEATURE:
<221> NAME/KEY: misc_feature
<222> LOCATION: (15)..(15)
<223> OTHER INFORMATION: n is a, c, g, or t

<400> SEQUENCE: 6

gtngaygart ayggnaaycc                                                  20


<210> SEQ ID NO 7
<211> LENGTH: 23
<212> TYPE: DNA
<213> ORGANISM: Artificial
<220> FEATURE:
<223> OTHER INFORMATION: Antisense primer for Forsythia DNA.

<400> SEQUENCE: 7

aryttytcyt tdatyttrtc cat                                              23


<210> SEQ ID NO 8
<211> LENGTH: 32
<212> TYPE: DNA
<213> ORGANISM: Artificial
<220> FEATURE:
<223> OTHER INFORMATION: Full length tea dehydrin primer.

<400> SEQUENCE: 8

aaaaagcagg cttcatggca cataacagca ac                                    32


<210> SEQ ID NO 9
<211> LENGTH: 34
<212> TYPE: DNA
<213> ORGANISM: Artificial
<220> FEATURE:
<223> OTHER INFORMATION: Full length tea dehydrin primer.

<400> SEQUENCE: 9

agaaagctgg gttttattta ttagtggtgg tgtg                                  34


<210> SEQ ID NO 10
<211> LENGTH: 33
<212> TYPE: DNA
<213> ORGANISM: Artificial
<220> FEATURE:
<223> OTHER INFORMATION: Primer for truncated tea dehydrin (122-201) of
      Seq ID 1

<400> SEQUENCE: 10

aaaaagcagg cttcatggag gatgatggtc aag                                   33


<210> SEQ ID NO 11
<211> LENGTH: 32
<212> TYPE: DNA
<213> ORGANISM: Artificial
```

-continued

```
<220> FEATURE:
<223> OTHER INFORMATION: Primer for truncated tea dehydrin (163-201) of
      Seq ID 1

<400> SEQUENCE: 11

aaaaagcagg cttcatggca gccaccaccg gt                                     32


<210> SEQ ID NO 12
<211> LENGTH: 36
<212> TYPE: DNA
<213> ORGANISM: Artificial
<220> FEATURE:
<223> OTHER INFORMATION: Primer for Forsythia suspensa dehydrin.

<400> SEQUENCE: 12

aaaaagcagg cttcctgcac tactgaacaa acttag                                 36


<210> SEQ ID NO 13
<211> LENGTH: 36
<212> TYPE: DNA
<213> ORGANISM: Artificial
<220> FEATURE:
<223> OTHER INFORMATION: Primer for Forsythia suspensa dehydrin.

<400> SEQUENCE: 13

agaaagctgg gttcataaac tcgactcaga cgcatg                                 36


<210> SEQ ID NO 14
<211> LENGTH: 8
<212> TYPE: PRT
<213> ORGANISM: Artificial
<220> FEATURE:
<223> OTHER INFORMATION: Consensus Sequence

<400> SEQUENCE: 14

Lys Ile Lys Glu Lys Leu Pro Gly
1               5


<210> SEQ ID NO 15
<211> LENGTH: 8
<212> TYPE: PRT
<213> ORGANISM: Artificial sequence
<220> FEATURE:
<223> OTHER INFORMATION: Concensus sequence
<220> FEATURE:
<221> NAME/KEY: MISC_FEATURE
<222> LOCATION: (4)..(4)
<223> OTHER INFORMATION: Xaa is Glu or Asp
<220> FEATURE:
<221> NAME/KEY: MISC_FEATURE
<222> LOCATION: (6)..(6)
<223> OTHER INFORMATION: Xaa is Leu or Ile

<400> SEQUENCE: 15

Lys Ile Lys Xaa Lys Xaa Pro Gly
1               5


<210> SEQ ID NO 16
<211> LENGTH: 8
<212> TYPE: PRT
<213> ORGANISM: Artificial Sequence
<220> FEATURE:
<223> OTHER INFORMATION: Concensus Sequence
<220> FEATURE:
<221> NAME/KEY: misc_feature
<222> LOCATION: (4)..(4)
<223> OTHER INFORMATION: Xaa is Glu or Asp
<220> FEATURE:
<221> NAME/KEY: misc_feature
```

<222> LOCATION: (6)..(6)
<223> OTHER INFORMATION: Xaa is Leu or Ile or Thr or Val
<220> FEATURE:
<221> NAME/KEY: misc_feature
<222> LOCATION: (7)..(7)
<223> OTHER INFORMATION: Xaa isPro or His or Ser

<400> SEQUENCE: 16

Lys Ile Lys Xaa Lys Xaa Xaa Gly
1 5

<210> SEQ ID NO 17
<211> LENGTH: 15
<212> TYPE: PRT
<213> ORGANISM: Artificial Sequence
<220> FEATURE:
<223> OTHER INFORMATION: Concensus sequence K branch
<220> FEATURE:
<221> NAME/KEY: misc_feature
<222> LOCATION: (4)..(4)
<223> OTHER INFORMATION: Xaa is Gly or Ser
<220> FEATURE:
<221> NAME/KEY: misc_feature
<222> LOCATION: (5)..(5)
<223> OTHER INFORMATION: Xaa is Ile or Val or Met or Leu or Phe
<220> FEATURE:
<221> NAME/KEY: misc_feature
<222> LOCATION: (6)..(6)
<223> OTHER INFORMATION: Xaa is Met or Leu or Val
<220> FEATURE:
<221> NAME/KEY: misc_feature
<222> LOCATION: (7)..(7)
<223> OTHER INFORMATION: Xaa is ASP or Glu
<220> FEATURE:
<221> NAME/KEY: misc_feature
<222> LOCATION: (11)..(11)
<223> OTHER INFORMATION: Xaa is Glu or Asp
<220> FEATURE:
<221> NAME/KEY: misc_feature
<222> LOCATION: (13)..(13)
<223> OTHER INFORMATION: Xaa is Leu or Ile

<400> SEQUENCE: 17

Glu Lys Lys Xaa Xaa Xaa Xaa Lys Ile Lys Xaa Lys Xaa Pro Gly
1 5 10 15

<210> SEQ ID NO 18
<211> LENGTH: 10
<212> TYPE: PRT
<213> ORGANISM: Artificial Sequence
<220> FEATURE:
<223> OTHER INFORMATION: Short peptide with homology to dehydrin
<220> FEATURE:
<221> NAME/KEY: misc_feature
<222> LOCATION: (2)..(2)
<223> OTHER INFORMATION: Xaa is Asp or Glu

<400> SEQUENCE: 18

Thr Xaa Glu Tyr Gly Asn Pro Val Gln His
1 5 10

<210> SEQ ID NO 19
<211> LENGTH: 7
<212> TYPE: PRT
<213> ORGANISM: Artificial Sequence
<220> FEATURE:
<223> OTHER INFORMATION: Y segment dehydin domain
<220> FEATURE:
<221> NAME/KEY: misc_feature
<222> LOCATION: (1)..(1)
<223> OTHER INFORMATION: Xaa is Thr or Val

<400> SEQUENCE: 19

-continued

```
Xaa Asp Glu Tyr Gly Asn Pro
1               5


<210> SEQ ID NO 20
<211> LENGTH: 15
<212> TYPE: PRT
<213> ORGANISM: Artificial Sequence
<220> FEATURE:
<223> OTHER INFORMATION: Designed for K domain

<400> SEQUENCE: 20

Glu Lys Lys Gly Ile Met Asp Lys Ile Lys Glu Lys Leu Pro Gly
1               5                   10                  15
```